US010456447B2

(12) United States Patent
Rabinovich et al.

(10) Patent No.: US 10,456,447 B2
(45) Date of Patent: Oct. 29, 2019

(54) THERAPEUTIC MODULATION OF SKIN IMMUNE SYSTEM WITH GAL-7

(71) Applicant: CONSEJO NACIONAL DE INVESTIGACIONES CIENTÍFICAS Y TÉCNICAS, Buenos Aires (AR)

(72) Inventors: Gabriel A. Rabinovich, Buenos Aires (AR); Juan Pablo Cerliani, Buenos Aires (AR); Nicolás Alejandro Pinto, Buenos Aires (AR)

(73) Assignee: Consejo Nacional de Investigacions Cientificas y Técnicas, Buenos Aires (AR)

( * ) Notice: Subject to any disclaimer, the term of this patent is extended or adjusted under 35 U.S.C. 154(b) by 0 days.

(21) Appl. No.: 15/725,432

(22) Filed: Oct. 5, 2017

(65) Prior Publication Data

US 2018/0110830 A1    Apr. 26, 2018

Related U.S. Application Data

(60) Provisional application No. 62/404,300, filed on Oct. 5, 2016.

(51) Int. Cl.
| | | |
|---|---|---|
| *A61K 38/16* | (2006.01) | |
| *A61K 39/00* | (2006.01) | |
| *A61K 38/17* | (2006.01) | |
| *A61K 9/00* | (2006.01) | |
| *A61P 29/00* | (2006.01) | |
| *A61P 17/06* | (2006.01) | |
| *A61K 9/06* | (2006.01) | |

(52) U.S. Cl.
CPC ........ *A61K 38/1732* (2013.01); *A61K 9/0014* (2013.01); *A61K 9/06* (2013.01); *A61P 17/06* (2018.01); *A61P 29/00* (2018.01)

(58) Field of Classification Search
CPC .................................................... A61K 38/17
See application file for complete search history.

(56) References Cited

U.S. PATENT DOCUMENTS

| | | | | | |
|---|---|---|---|---|---|
| 6,800,609 | B1 * | 10/2004 | Mehul | ........................ | A61K 8/64 424/134.1 |
| 2006/0189514 | A1 * | 8/2006 | Panjwani et al. | ...... | A61K 38/17 514/8 |

OTHER PUBLICATIONS

Wikapedia search, Jul. 2018.*
Abrams et al., "Blockade of T lymphocyte costimulation with cytotoxic T lymphocyte associated antigen 4-immunoglobulin (CTLA4Ig) reverses the cellular pathology of psoriatic plaques, including the activation of keratinocytes, dendritic cells, and endothelial cells," J Exp Med.2000; 192:681-94.
Allan et al., "Inducible reprogramming of human T cells into Treg cells by a conditionally active form of FOXP3," Eur J Immunol. 2008;38(12):3282-9.
Awasthi et al. "Cutting edge: IL-23 receptor gfp reporter mice reveal distinct populations of IL-17-producing cells," J Immunol. 2009;182(10):5904-8.
Baadsgaard et al., "The role of the immune system in the pathogenesis of psoriasis," J Invest Dermatol. 1990;95(5):32S-4S.
Baran et al., "Expression of p53 protein in psoriasis," Acta dermatovenerologica Alpina, Panonica, et Adriatica. 2005;14(3):79-83.
Bernerd et al., "Galectin-7 overexpression is associated with the apoptotic process in UVB-induced sunburn keratinocytes," Proc Natl Acad Sci USA. 1999;96(20):11329-34.
Biron-Pain et al., "Expression and functions of galectin-7 in human and murine melanomas," PloS ONE. 2013;8(5)e63307:1-10.
Bursch et al., "Identification of a novel population of Langerin+ dendritic cells," J Exp Med. 2007;204(13):3147-56.
Cao et al., "Galectins-3 and -7, but not galectin-1, play a role in re-epithelialization of wounds," J. Biol. Chem. 2002;277, 42299-42305.
Cao et al., "Galectin-7 as a potential mediator of corneal epithelial cell migration," Arch. Ophthalmol . . . 2003; 121, 82-86.
Caruso et al., :Involvement of interleukin-21 in the epidermal hyperplasia of psoriasis, Nat Med 2009;15(9):1013-5.
Ciric et al., "IL-23 drives pathogenic IL-17-producing CD8+ T cells," J Immunol. 2009;182(9):5296-305.
Cooper, "Galectinomics: finding themes in complexity," Biochim Biophys Acta. 2002;1572(2-3):209-31.
Croc et al., "Glycosylation-Dependent Lectin-Receptor Interactions Preserve Angiogenesis in Anti-VEGF Refractory Tumors," Cell 2014;156(4):744-58.
de Lafaille et al., "Natural and adaptive foxp3+ regulatory T cells: more of the same or a division of labor?," Immunity. 2009;30(5):626-35.
Delgado et al. "Modulation of endothelial cell migration and angiogenesis: a novel function for the 'tandem-repeat' lectin galectin-8," FASEB J 2011;25(1):242-54.
Demetriou et al., "Negative regulation of T-cell activation and autoimmunity by Mgat5 N-glycosylation," Nature. 2001;409(6821):733-9.
Edelson et al., "Peripheral CD103+ dendritic cells form a unified subset developmentally related to CD8alpha+ conventional dendritic cells," J Exp Med 2010;207(4):823-36.
Gagliani et al., "Coexpression of CD49b and LAG-3 identifies human and mouse T regulatory type 1 cells," Nat Med. 2013 19(6):739-46.
Gendronneau et al., "Galectin-7 in the control of epidermal homeostasis after injury," Mol Biol Cell. 2008;19(12):5541-9.
Goedkoop et al. "Alefacept therapy reduces the effector T-cell population in lesional psoriatic epidermis," Arch Dermatol Res 2004;295(11):465-73.

(Continued)

*Primary Examiner* — Maryam Monshipouri
(74) *Attorney, Agent, or Firm* — Eversheds Sutherland (US) LLP

(57) ABSTRACT

This invention provides methods of modulating immune responses in the skin. The invention further provides methods of treatment for psoriasis, epidermal and dermal inflammation, and associated dermal immunity conditions by administering to an individual patient in need an effective amount of Gal-7, functional fragments of Gal-7, or agonists of Gal-7.

5 Claims, 15 Drawing Sheets

Specification includes a Sequence Listing.

(56) References Cited

OTHER PUBLICATIONS

Ghoreishi et al., :Expansion of antigen-specific regulatory T cells with the topical vitamin d analog calcipotriol, J Immunol. 2009;182(10):6071-8.

Hemmi et al., "Skin antigens in the steady state are trafficked to regional lymph nodes by transforming growth factor-beta1-dependent cells," Int Immunol 2001;13(5):695-704.

Honda et al., Update of immune events in the murine contact hypersensitivity model: toward the understanding of allergic contact dermatitis, J Invest Dermatol. 2013;133(2):303-15.

Igyarto et al., :Langerhans cells suppress contact hypersensitivity responses via cognate CD4 interaction and langerhans cell-derived IL-10, J Immunol 2009;183(8):5085-93.

Ilarregui et al., "Tolerogenic signals delivered by dendritic cells to T cells through a galectin-1-driven immunoregulatory circuit involving interleukin 27 and interleukin 10," Nat Immunol 2009;10(9):981-91.

Kaplan et al, "Epidermal langerhans cell-deficient mice develop enhanced contact hypersensitivity," Immunity. 2005;23(6):611-20.

Kissenpfennig et al., "Dynamics and function of Langerhans cells in vivo: dermal dendritic cells colonize lymph node areas distinct from slower migrating Langerhans cells," Immunity. 2005;22(5):643-54.

Kopitz et al., "Flomodimeric galectin-7 (p53-induced gene 1) is a negative growth regulator for human neuroblastoma cells," Oncogene. 2003;22(40):6277-88.

Leffler et al., "Introduction to galectins," Glycoconjugate J 2004;19(7-9):433-40.

Lew et al., "Psoriasis vulgaris: cutaneous lymphoid tissue supports T-cell activation and "Type 1" inflammatory gene expression," Trends Immunol 2004;25(6):295-305.

Liu et al., "Galectins as modulators of tumour progression," Nat Rev Cancer. 2005;5(1):29-41.

Madsen et al., "Cloning, expression, and chromosome mapping of human galectin-7," J Biol Chem. 1995;270(11):5823-9.

Magnaldo et al. "Galectin-7, a human 14-kDa S-lectin, specifically expressed in keratinocytes and sensitive to retinoic acid." Dev Biol, 1995, 168(2): 259-271.

Magnaldo et al., "Galectin-7, a marker of all types of stratified epithelia," Differentiation. 1998;63(3):159-68.

Marble et al., "Targeting TNFalpha rapidly reduces density of dendritic cells and macrophages in psoriatic plaques with restoration of epidermal keratinocyte differentiation," J Dermatoll Sci. 2007;48(2):87-101.

Markowska et al., "Galectin-3 is an important mediator of VEGF- and bFGF-mediated angiogenic response," J Exp Med. 2010;207(9):1981-93.

Marth et al., "Mammalian glycosylation in immunity," Nat Rev Immunol. 2008;8(11):874-87.

Martin et al., "The emerging role of IL-17 in the pathogenesis of psoriasis: preclinical and clinical findings," J Invest Dermatol. 2013;133(1):17-26.

Noordegraaf et al., "Functional redundancy of Langerhans cells and Langerin+ dermal dendritic cells in contact hypersensitivity," J Invest Dermatol 2010;130(12):2752-9.

Rabinovich et al., "An emerging role for galectins in tuning the immune response: lessons from experimental models of inflammatory disease, autoimmunity and cancer," Scand J Immunol. 2007;66(2-3):143-58.

Rabinovich et al., "Functions of cell surface galectin-glycoprotein lattices," Curr Opin Struct Biol 2007;17(5):513-20.

Rabinovich et al., "Turning 'sweet' on immunity: galectin-glycan interactions in immune tolerance and inflammation," Nat Rev Immunol. 2009;9(5):338-52.

Roncarolo et al., "Type 1 T regulatory cells," Immunol Rev 2001;182:68-79.

Sakaguchi "Naturally arising Foxp3-expressing CD25+CD4+ regulatory T cells in immunological tolerance to self and non-self," Nat Immunol. 2005;6(4):345-52.

Salatino et al., "Galectin-1 as a potential therapeutic target in autoimmune disorders and cancer," Exp Opin Biol Ther 2008;8(1):45-57.

Saussez et al., "Galectin-7," Cell Moll Life Sci. 2006;63(6):686-97.

Sutton et al., "Interleukin-1 and IL-23 induce innate IL-17 production from gammadelta T cells, amplifying Th17 responses and autoimmunity," Immunity. 2009;31(2):331-41.

Tan et al., "Contact dermatitis: allergic and irritant," Clin Dermatol. 2014;32(1):116-24.

Thijssen et al., "Galectin-1 is essential in tumor angiogenesis and is a target for antiangiogenesis therapy," Proc Natl Acad Sci USA 2006;103(43):15975-80.

Timmons et al., "Expression of galectin-7 during epithelial development coincides with the onset of stratification," Int J Dev Biol 1999;43(3):229-35.

Ueda et al., Suppression of tumor growth by galectin-7 gene transfer, Cancer Res 2004;64(16):5672-6.

Valencia et al., CD4+CD25+FoxP3+ regulatory T cells in autoimmune diseases, Nat Clin Pract Rheumatol 2007;3(11):619-26.

Van Belle et al., IL-22 is required for imiquimod-induced psoriasiform skin inflammation in mice, J Immunol. 2012;188(1):462-9.

Van Kooyk et al., "Protein-glycan interactions in the control of innate and adaptive immune responses," Nat immunol 2008;9(6):593-601.

Vignali et al., "How regulatory T cells work," Nat Rev Immunol 2008;8(7):523-32.

Yang et al., "Galectins: structure, function and therapeutic potential," Expert Rev Mol Med. 2008;10. doi:10.1017/S1462399408000719.

Wang et al., "Langerin expressing cells promote skin immune responses under defined conditions," J immunol 2008;180(7):4722-4727.

* cited by examiner

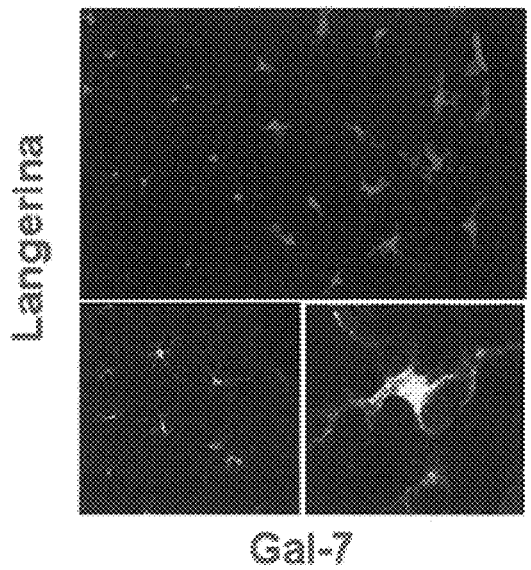 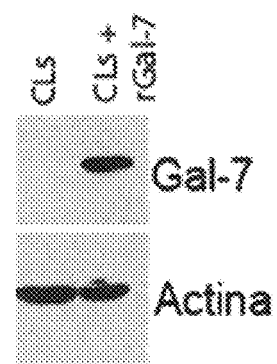
FIG. 3A              FIG. 3B
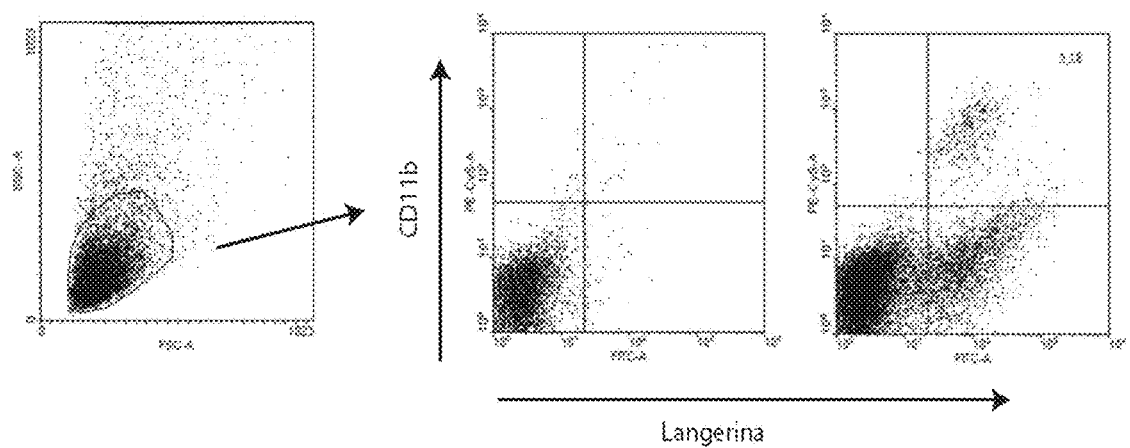
FIG. 4A

SEQUENCE LISTING

<160> NUMBER OF SEQ ID NOS: 1

<210> SEQ ID NO 1
<211> LENGTH: 136
<212> TYPE: PRT
<213> ORGANISM: Homo sapiens

<400> SEQUENCE: 1

```
Met Ser Asn Val Pro His Lys Ser Ser Leu Pro Glu Gly Ile Arg Pro
1               5                   10                  15

Gly Thr Val Leu Arg Ile Arg Gly Leu Val Pro Pro Asn Ala Ser Arg
            20                  25                  30

Phe His Val Asn Leu Leu Cys Gly Glu Glu Gln Gly Ser Asp Ala Ala
        35                  40                  45

Leu His Phe Asn Pro Arg Leu Asp Thr Ser Glu Val Val Phe Asn Ser
    50                  55                  60

Lys Glu Gln Gly Ser Trp Gly Arg Glu Glu Arg Gly Pro Gly Val Pro
65                  70                  75                  80

Phe Gln Arg Gly Gln Pro Phe Glu Val Leu Ile Ile Ala Ser Asp Asp
                85                  90                  95

Gly Phe Lys Ala Val Val Gly Asp Ala Gln Tyr His His Phe Arg His
            100                 105                 110

Arg Leu Pro Leu Ala Arg Val Arg Leu Val Glu Val Gly Gly Asp Val
            115                 120                 125

Gln Leu Asp Ser Val Arg Ile Phe
    130                 135
```

THERAPEUTIC MODULATION OF SKIN IMMUNE SYSTEM WITH GAL-7

CROSS REFERENCE TO RELATED APPLICATION

This application claims priority benefit of U.S. Provisional Application No. 62/404,300 filed Oct. 5, 2016. The entire contents of which is hereby incorporated by reference herein.

FIELD OF THE INVENTION

The disclosure generally relates to uses of galectins, such as Gal-7, in methods for modulating an immune response in the skin and treatment methods for conditions that benefit from regulation of the inflammatory immune response.

SEQUENCE LISTING

The instant application contains a Sequence Listing which has been submitted electronically in ASCII format and is hereby incorporated by reference in its entirety. Said ASCII copy, created on Oct. 4, 2017, is named 33858-0022_SL.txt and is 1,527 bytes in size.

BACKGROUND

There are numerous inflammatory skin diseases, which prompt millions of patients to visit dermatology clinics annually. In most cases, cutaneous pathologies are caused by irritant, and even pathogen, agents. Among these diseases, however, there are some where homeostasis of the immune system is compromised; psoriasis, considered a possibly autoimmune disease, and allergic contact dermatitis (ACD) are two examples of this type of pathology.

Psoriasis is a chronic inflammatory skin pathology affecting between 2-3% of the world population. In most clinical cases, 20% of these patients may develop rheumatoid arthritis, complicating their quality of life. The symptomatology of this disease transcends merely esthetic concerns involving the formation of erythematous plaques in the skin, affecting elbow and knee joints, posing complications to the patient's clinical picture. This variant of the disease is usually diagnosed erroneously because it has a similar symptomatology to arthritis.

On the other hand, contact dermatitis is one of the world's most common work-related diseases, as it is caused by prolonged exposure to certain commonly non-immunogenic molecules (hapten). In such cases, constant exposure to the hapten may trigger highly inflammatory hypersensitive events since this molecule can covalently bond to the patient's own proteins. Covalent bonding between the patient's own protein and the hapten generates a new antigen that now does have immunogenic properties inducing a more powerful immune response.

In the case of psoriasis and ACD, even though they are pathologies with different etiologies, they do have the same cellular networks, such as dendritic cells residing in the skin (Langerhans cells, dermal cells), circulating T lymphocytes, macrophages, etc., which collectively induce a circuit of cellular and humoral components that converge in inflammatory processes triggered by immunogenic stimuli.

The skin is the most extensive organ of the human body. In some areas, it is 0.5 mm thick, as in the eyelids, whereas in other parts, as in the palms of the hands or soles of the feet, it reaches a thickness of up to 5 mm. Histologically, the skin is subdivided into three layers: 1) the epidermis, which is the outermost layer; 2) the dermis, or the middle layer; and 3) the hypodermis, which is the deepest layer, basically made up of subcutaneous fatty tissue.

The skin is, along with the mucous epithelium, the first physical defense barrier against the entry of different microorganisms, many of which can be pathogenic. In particular, the epidermis maintains direct contact with the external environment and consists of a stratified epithelium, made up of basal cells involved in tissue regeneration and more differentiated suprabasal cells, known as keratinocytes. As cell differentiation progresses, the keratinocytes express high concentrations of keratin. This protein gives cells the capacity to resist mechanical and chemical abrasion, and in addition provide great impermeability to the epidermis. When keratinocytes reach a high concentration of keratin and lipids in their cytosol, they lose their nuclei and die, forming the stratum corneum.

Keratinocytes can be activated through their cytokine receptors or pathogen recognition receptors (PRR) and secrete a wide range of cytokines to the microenvironment, for example, interleukin 1 (IL-1), IL-6, TNF-$\alpha$, TGF-$\beta$1, IFN-$\gamma$, chemokines, such as IL-8, and lectins, such as Galectin (Gal)-1, -3, and -7.

All these molecules secreted by the keratinocytes can modulate cell activity in the resident skin immune system, such as Langerhans Cells (LCs), polymorphonuclear cells (PMNs), and even T cells crossing and migrating through this tissue.

T lymphocytes are key components in the adaptive immune response, which is evident three days after innate immune response mechanisms are activated. At this stage, dendritic cells (DCs) act as a link between the innate immune response and the adaptive immune response. LCs are immature antigen-presenting cells, residing in the epidermis, and like all immature dendritic cells, they have a high endocytic capacity and a low antigen-presenting ability. Nevertheless, upon invasion by a pathogen, resident dendritic cells endocyte the pathogen, maturate, and migrate to draining lymph nodes. This maturation consists in the presentation of endocyte antigens (Ag) within the context of a class II major histocompatibility complex (MHC II), which induces specific activation of virgin T lymphocytes in the secondary lymphatic organs. Activation of the lymphocytes requires three specific signals: 1) one between the antigen/MHC II and T cell receptor (TCR); 2) interaction between CD28 co-receptor (T cell) and CD80/CD86 co-receptor (APC); and, finally, 3) the microenvironment of cytokines secreted by the APC. This last signal is mainly responsible for the type of effector T response. After antigen presentation, lymphocyte T $\alpha\beta$ CD4$^+$ can acquire different sub-class of T helper cells: T helper 1 (Th1), Th2, Th9, Th17, Th22, and regulatory T cells.

The Th1 cells are a subtype of T-lineage lymphocytes, which are differentiated from naïve T cells in the presence of IL-12 and IL-18 secreted from the antigen-presenting cell. These lymphocytes are characterized for secreting high levels of IFN-$\gamma$, a potent activator of phagocytic/degradative activity in macrophages, known as the "oxidative burst." This activation determines that macrophages increase the expression of the CD80 and CD86 molecules, MHC I and II molecules, CD40, chemokines (IL-8 and MCP-1), inflammatory cytokines (IL-1 and TNF-$\alpha$), and oxygen reactive species (superoxide anion, nitrogen oxide [NO], etc.).

In particular, participation of Th1 lymphocytes has been described in chronic inflammatory processes, whereas Th17 lymphocytes are the cells that maintain the inflammatory foci during the chronic stage of the pathology. The Th17 cells are characterized for secreting IL-17 (present as A or F isoforms), which acts as a chemokine of neutrophils, and IL-22. This T response stimulates neutrophilia (by secretion of G-CSF) and neutrophil recruitment at the infection site. It also stimulates macrophages to produce proinflammatory cytokines, stimulates TNF-α secretion, induces metalloproteinase secretion, and promotes the production of mucus as well as antimicrobial peptides, chemokines, and IL-6. This last interleukin, along with TGF-β1, promote cell differentiation to Th17 profile in T cells activated by IL-2. In addition, IL-23 makes the activated Th17 expand and produce more IL-17 and IL-6. In this regard, a T cell subtype, the Th22 lymphocyte, specific producer of IL-22, has been described recently promoting proliferation of keratinocytes. This cytokine is mainly responsible for the formation of erythematous plaques characteristic of psoriasis.

Lastly, regulatory T cells (Tregs) are a subtype of lymphocytes of T αβ lineage particularly focused on negatively regulating immune response. There are two types of Tregs, natural Tregs (nTregs) and inducible Tregs (iTregs) (Sakaguchi et al., 2005). The nTregs mature in the thymus and present markers characteristic of CD4, $CD25^{high}$ and the Foxp3 transcription factor. On the other hand, iTregs are differentiated in secondary lymphoid organs from naïve $CD4^+$ $CD25^-$ T cells in the presence of TGF-β1 and are also $CD4^+$ $CD25^{high}Foxp3^+$. Moreover, a subpopulation of iTRegs known as Tr1 has been described. Tr1 is differentially generated in the presence of IL-27, does not express the Foxp3 transcription factor ($Foxp3^-$) (Roncarolo et al., 2001, Ilarregui et al., 2009) but selectively expresses the LAG-3 and CD49d markers (Gagliani et al., 2013). Numerous studies based on selectively eliminating this population or blocking their activity suggest that Tregs basically participate in promoting homeostasis of the immune response (Valencia and Lipsky, 2007; Vignali et al., 2008).

Tregs express CTLA-4, FAS-L or secrete IL-10, IL-35, and TGF-β1, that can induce cell death or anergy of effector T cells, contributing to the resolution of the immune response and to the maintenance of peripheral tolerance (Curotto de Lafaille and Lafaille, 2009). Thus, differentiation of naïve T cells to a regulatory T lineage in patients with autoimmune diseases such as psoriasis could have the capacity of resolving the inflammatory process. Accordingly, stimulation of the skin's immune cells with molecules that positively modulate the differentiation of T naïve to regulatory T cells can be an attractive treatment option for chronic skin pathologies.

In psoriasis pathologies, keratinocytes have an unregulated mechanism of proliferation, apoptosis, and differentiation promoting the production of erythematous plaques, acanthosis (increase in epidermal thickness) and parakeratosis (an incomplete keratinization characterized by the retention of nuclei in the stratum corneum) (Baadsgaard et al., 1990). Furthermore, the initial cause that triggers the pathology and the circuits leading to their resolution are unknown (Abrams et al., 2000; Goedkoop et al., 2004; Lew et al., 2004). The general consensus on this autoimmune disease states that there are genetic factors associated to a possible initial infection that contribute to triggering this chronic inflammatory skin response.

One such consequence of the parakeratosis process is a reduction in Gal-7 expression (a lectin preferentially expressed in keratinocytes) in the deepest layers of the epidermis (Magnaldo et al., 1995), as a symbol of a deficiency in the epithelial stratification. This deficiency in epidermal differentiation is accompanied by an important compromise in the inflammatory infiltrate of Th1 and Th17 lymphocytes, macrophages, and DCs. In the acute stage, Th1 lymphocytes are the first recruited in the skin, and by secreting IFN-γ they contribute to the inflammatory environment characteristic of the first stage of the pathology. In the subsequent chronic stage, however, the Th1 lymphocyte infiltrate diminishes, and Th17 cells overcome in this second stage. The Th17 lymphocytes located in the affected tissue secrete high concentrations of IL-17, -21, and -22, although the greater source for the production of IL-22 is represented by the recently identified Th22 lymphocyte subpopulation. There is a difference between the mouse model and humans. The presence of Th22 is largely documented in patients with psoriasis, but it was not possible to characterize this T lymphocyte subpopulation in mice. In animals, Th17 lymphocytes contribute as the main source of IL-22 (Awasthi et al., 2009; Ciric et al., 2009; Sutton et al., 2009).

Recently, blocking anti-IL-21 antibodies were observed to reduce inflammation, infiltration of the immune system cells, and proliferation of keratinocytes in experimental murine models that had received xenotransplants from psoriatic patients (Caruso et al., 2009). At the same time, during the course of the disease, an increased expression of the p53 protein was observed in patient lesions (Baran et al., 2005). Interestingly, Gal-7 is a lectin that was described and identified as a p53-regulated protein (Kopitz et al., 2003).

In addition, TNF-α, a proinflammatory cytokine involved in the activation and migration of LCs, is an essential factor in the development of this pathology (Marble et al., 2007). Several clinical trials have shown that TNF-α blocking produces a significant improvement in patients with psoriasis. The underlying mechanism of this therapeutic effect is still under controversy, but recent studies have revealed that treatment with ETANERCEPT, a soluble TNF-α-blocking receptor, produces a rapid decrease in inflammation and an increase in the apoptosis of dermal dendritic cells (DCs).

Contact Hypersensitivity (CHS) is an inflammatory skin model that is widely used in studies on inflammatory skin diseases because the induced immunological mechanisms are similar to the ones manifest in human allergic contact dermatitis (ACD). In short, ACD has a number of well-established phases, the first of which is the initiation or sensitization phase. Haptens are low molecular weight molecules that have no immunogenic capacity and act as a sensitizing molecule during this phase. Moreover, haptens can undergo modifications in the skin, such as covalent bonding to the patient's proteins, thus acquiring immunogenic capacity (called carrier proteins).

At the initial phase of sensitization, the DCs, now activated by the new antigen (hapten-carrier), mature and migrate to the lymph nodes, presenting the antigen to T cells. The activated T lymphocytes proliferate and migrate from the lymph nodes, remaining in circulation until they enter into contact with the hapten-carrier within the context of the MHC II in an antigen-presenting cell.

The second phase or inflammatory phase is triggered by a subsequent stimulus with the allergen and it can be divided in two stages: an early stage (2-hour post re-stimulation with the allergen) and a late stage (24 hours after re-stimulation), each one of them is characterized by a specific cellular and humoral profile. Finally, 48 hours post-contact with the allergen, the inflammation decreases due to the activity of the regulatory T cells (Tregs), $CD4^+$, $CD25^+$, $FoxP3^+$, as well as IL-10-secreting Tr1 cells (Allan et al., 2008). The regulatory capacity of these cells is manifest both at the level of the draining lymph nodes as well as at the periphery of the skin, where they inhibit clonal expansion of T $CD8^+$ lymphocytes (Fas-FasL pathway and the interaction between CTLA-4 and CD80/CD86) (Tan et al., 2014).

By contrast, Irritant Contact Dermatitis (ICD) has no first sensitization phase as in CHS. Recent studies show that LCs migrates from the skin to the lymph nodes after topical application of an irritant. At the same time, the infiltrate responds (resident CD4+ and CD8+) to stress and chemokines secreted by the keratinocytes of the epidermis, as well as dermal fibroblasts. These fibroblasts are exposed to the irritant because epidermal irritation alters cutaneous permeability, enabling the inflammatory agent to reach the dermis. Thus, both ACD as well as ICD share in great measure the cellular and humoral components present in the immune response during the inflammatory process.

Furthermore, the presence of inflammatory cytokines on Th1 and Th17 cells has been observed during cutaneous irritation; they are also present in the skin of psoriatic patients. Therefore, the use of both experimental models might allow for elucidating the immunological circuits operating during the skin's inflammatory response.

Even though both inflammatory pathologies are considerably different as regards the factor that triggers immune response, the type of infiltrate that characterizes them as well as the duration and magnitude of the inflammatory process have something in common: the DCs that capture and present antigens to T cells are intimately tied to the onset of the pathologies.

Recent studies, however, indicate that skin DCs can act dependent on the microenvironment inducing T lymphocytes to either inflammatory profiles (Th1, Th17, etc.) or tolerogenic or anti-inflammatory profiles (iTreg, Tr1).

Langerhans Cells (LCs) are professional antigen-presenting cells (CPA) located in the basal and suprabasal regions of the epidermis, where they interact continuously with the keratinocytes. The LCs come from bone marrow, have a characteristic CD1+CD34+Langerin+ phenotype, and are bound to the keratinocytes by E-cadherin-mediated bonds, forming a network of antigen-presenting cells in the epidermis.

LCs are not the only Langerin+/− antigen-presenting cells of the skin. In addition, there are Langerin+ dendritic cells (DCs) and Langerin⁻ dermal DCs in the dermis, complicating the scenario even more in the attempt to identify who triggers the immune response with a specific stimulus and who regulates negatively the response. Pioneer work sustained that all skin DCs were responsible for capturing foreign antigens, then migrating to lymph nodes and presenting the antigens to T lymphocytes (LT) in order to trigger an adequate immune response (Hemmi et al., 2001). In the past decade, however, this premise was found not to be as conclusive as originally proposed; instead, it is now known that there is a complex mechanism where each DC subpopulation in the skin may play a specific role.

In turn, the same DC population is capable of participating in either inflammatory or anti-inflammatory, dependent on the prevailing cytokines in the microenvironment during the activation process. This microenvironment is determined mainly by the cytokines and activation of the LCs can modify its physiology and the glycosylation pattern (or glycophenotype) of the membrane proteins. Various studies have shown that differential glycosylation of proteins plays a fundamental role in the functioning and homeostasis of the immune system (Demetriou et al., 2001) as it affects interactions between cells, and between cells and proteins present in the extracellular matrix. Indeed, the glycome of a cell can modify the specific bond of membrane glycoproteins to proteins present in the extracellular environment; activate signaling cascades; or retain receptors in the membrane, thus modifying the type of response of such cells.

The enzymes that synthesize glycan structure and the remodeling of saccharide that constitute the glycoproteins are called glycosyltransferases and glycosidases (Marth and Grewal, 2008). These enzymes are part of the rough endoplasmic reticulum and the Golgi apparatus, where saccharides are incorporated and eliminated sequentially. Moreover, this biosynthesis process is finely regulated and coordinated by chaperone proteins that, in conjunction with the glycosyltransferases and glycosidases, synthesize the final glycoprotein structure (Rabinovich and Toscano, 2009; Van Kooyk and Rabinovich, 2008). These glycans play essential roles in cell physiology, as they are involved in cell adhesion, migration, subcellular traffic, endocytosis, signal transduction, receptor activation, etc.

There are several checkpoints involved in the biosynthesis of specific glycoproteins. Nonetheless, the main mechanism for switching the glycophenotype consists in recycling protein by endocytosis and the subsequent synthesis of new molecules subject to the differential activity of glycosyltransferases and glycosidases regulated by different cellular stimuli.

Information codified in the glycome is decoded by different protein families called lectins or glycan-binding proteins. These molecules have a high affinity to different saccharide residues of cell surface glycoproteins. These lectins can also be divided into different groups according to their evolutionary structural relationship and their affinity to carbohydrates: 1) Siglecs (associated to the cell surface), 2) C-type Lectins (associated to the cell surface), and 3) Galectins (soluble molecules for intracellular and extracellular localization).

As mentioned before, the responsibility for decoding the biological information contained in the glycome lies, at least in part, in a group of proteins known as galectins (Leffler et al., 2004). These proteins present a preferential affinity to repeat units [Galβ1-4-NAcGlc] in both N- as well as O-glycans of the glycoprotein cell surface and extracellular matrix (Salatino et al., 2008). This bonding to glycosidic residues occurs through a carbohydrate recognition domain (CRD, approximately 130 amino acids) that is highly conserved in all its galectins (Cooper et al., 2002). In addition, depending on its biochemical structure, galectins are classified in three groups: "prototype galectins" (Gal-1, 2, 5, 7, 10, 11, 13, 14, y 15), "chimeric galectin" (Gal-3), and "tandem-repeat galectin" (Gal-4, 6, 8, 9, y 12) (Liu and Rabinovich 2005; Yang et al., 2008).

Galectins can be expressed in all animal species, and many of them are tissues and compartments specific. Recently, diverse intracellular and extracellular functions have been described (Rabinovich et al., 2007; Rabinovich and Toscano, 2009).

Even though these proteins are secreted by the cells and are mostly located in the extracellular environment, there is no peptide signal in their amino acid sequence. Consequently, their secretion is independent of the classic ER and Golgi apparatus pathways; on the other hand, these proteins are secreted by an a typical mechanism known as ectocytosis (Yang et al., 2008).

In recent years, this lectin family has been linked to various biological processes as regulators of homeostasis in the immune response (Rabinovich and Toscano, 2009), tumor progression (Liu and Rabinovich, 2005), and neovascularization (Cardenas Delgado et al., 2010; Markowska et al., 2010; Thijssen et al., 2006; Croci et al., 2014). Some galectins, such as Gal-1 and Gal-3, are expressed in a broad range of tissues, whereas other galectins have a more restricted expression pattern, such as Gal-4 in the gastrointestinal system, Gal-10 in eosinophils, Gal-12 in adipose tissue, and Gal-7 in keratinocytes.

Both Gal-7 as well as Gal-1 are expressed in keratinocytes and share their affinity to LacNAc repeats. However, affinity of Gal-1 to LacNAc terminal units is greater than Gal-7. Another important difference between these two proto-type galectins is that Gal-1 binding is sterically prevented when the oligosaccharide has sialic acid residue in the α2,6 terminal position (this is not so in the α2,3 sialylation position). On the other hand, neither of these two positions of the sialic acid residue modifies Gal-7 binding. In this sense, the differential binding capacity of these two lectins expressed by keratinocytes can induce different signaling pathways.

Gal-7, an endogenous lectin preferentially expressed on keratinocytes (Saussez and Kiss, 2006), was discovered simultaneously in two laboratories: one was studying genes that respond to retinoic acid (Madsen et al., 1995) and the other was looking for genes inducible by oncogen p53. Gal-7 is expressed in stratified epithelia and it has been claimed that Gal-7 might contribute to tissue homeostasis (Gendronneau et al., 2008). Nonetheless, it has been observed that this lectin is also expressed in the trachea and the ovary, two unstratified epithelia (Sao et al., 2002). This lectin is distributed in the cell-to-cell contact regions, particularly in the outermost layers of the epidermis, as well as in the esophagus epithelium, the oral cavity, the cornea, and Hassall's corpuscles in the thymus of mice, rats, and humans.

Even though the role of Gal-7 in tissue immunity has not been completely elucidated, various functions of this lectin regarding epithelial homeostasis have been described, under physiological as well as pathological conditions.

Cell Migration:

Using an in vivo model consisting of cornea lesions induced by UV radiation, topical treatment with recombinant Gal-3 (rGal-3) and recombinant Gal-7 (rGal-7) induced greater scarring of the lesions in relation to the different growth factors (Cao et al., 2002; Cao et al., 2003).

Apoptosis Regulation:

Given that one of the molecular mechanisms induced by Gal-1 binding to its specific ligands is the activation of the apoptosis pathway, the function of Gal-1, Gal-2, Gal-9, and Gal-7 as pro-apoptotic effectors has been studied in different cell models. In particular, in colon cancer DLD-1 cells, the p53-dependent apoptosis pathway evidenced an increase in Gal-7 expression, among other 7002 genes. In other related work, UVB radiation was shown to induce p53 expression on keratinocytes, leading to an increase in Gal-7 levels (Bernerd et al., 1999).

Effect on Tumor Progression:

The role of Gal-7, like in the majority of galectins, in tumor progression/development, is controversial. In certain tumor cell lines, it has anti-tumor effects, whereas in others, it has pro-tumor functions. Both in vivo and in vitro models have shown that DLD-1 tumor cells transfected with Gal-7 have a lower tumor growth rate independently of cell apoptosis (Ueda et al., 2003). This same anti-tumor property of Gal-7 has been observed in human neuroblastoma cells (Kopitz et al., 2003).

Tissue Differentiation Marker:

It has been claimed that Gal-7 may be used as a tissue differentiation marker given that, at the onset of its expression on keratinocytes, it coincides with the beginning of epidermal stratification (Magnaldo et al., 1995; Magnaldo et al., 1998; Timmons et al., 1999) and its level of expression is higher in areas of the skin where the epidermis is made up of a greater number of suprabasal cell layers.

SUMMARY OF THE INVENTION

This Summary is provided to introduce a selection of concepts that are further described herein. This Summary is not intended to identify key or essential features of the invention, nor is it intended to limit the scope of the invention.

The invention provides methods of prevention and treatment, methods for the manufacture of a medicament, and pharmaceutically acceptable compositions, for treating and preventing psoriasis and associated dermal immune conditions.

The invention provides a method for treating (including preventing) psoriasis and associated conditions comprising, administering to an individual in need thereof an effective amount of Gal-7, or a functional fragment of Gal-7, thereby treating the psoriasis and associated conditions. In embodiments, the administration of an effective amount of Gal-7, or a functional fragment of Gal-7, increases dermal regulatory T lymphocytes in the individual. In embodiments, the administration of an effective amount of Gal-7, or a functional fragment of Gal-7, activates Langerhans cells to stimulate T-cell differentiation to regulatory T lymphocytes in the individual.

The invention provides for modulation of the dermal immune system and the treatment of associated conditions selected from, for example, dermal inflammation, erythematous plaques, allergic contact dermatitis, parakeratosis, acanthosis, parakeratosis, autoimmune disease and psoriasis.

The invention also provides for the methods of treatment of psoriasis, dermal inflammation, and associated dermal immunity conditions as described above using an agonist of Gal-7 to stimulate the production or distribution of Gal-7 and the dermal immune system effects described herein.

The invention also provides for the methods of treatment of psoriasis, dermal inflammation, and associated dermal immunity conditions as described above using of an agent that mimics the interaction between Gal-7 and a natural binding partner of Gal-7.

The invention provides that Gal-7, or functional fragment of Gal-7, may be naturally occurring or synthetically produced. The Gal-7, or functional fragment of Gal-7, may be a recombinant protein. The recombinantly produced protein may be expressed and purified ex vivo for administration, or be produced in vivo via delivery to the patient of an encoding nucleic acid sequence.

These and other features, aspects, and advantages of the invention will become better understood with reference to the following description, examples, figures, and appended claims.

BRIEF DESCRIPTION OF THE DRAWINGS

The manner in which objectives of the present disclosure and other desirable characteristics may be obtained will become further evident from the following descriptions of the appended drawings.

FIGS. 3A-3B LC and Gal-7 Distribution: A) Images of skin segments dyed with anti-Langerin and anti-Gal-7 antibodies. The top image shows LC distribution in the skin forming a network. The lower left image shows the double staining for Langerin and Gal-7, whereas the lower right image magnifies an area of the left image, showing colocalization of markers. B) Image of a Western Blot membrane where LCs do not express Gal-7, but this protein can bond to the membrane glycans of LCs.

FIGS. 4A-4C Glycosylation of LCs and Binding to Gal-7: 4A) Diagrams of cell populations analyzed by cytometry, where CD11b+ and Langerin+ LCs are present in an epidermis disaggregate. 4B) LC cytometry of the glycophenotype with plant lectins; 4C) Binding assays of Gal-7 to LCs. A representative experiment is shown from a total of 5 with similar results.

DETAILED DESCRIPTION OF THE INVENTION

Figures 1A, 1B, 1C, 1D, 1E, 1F:
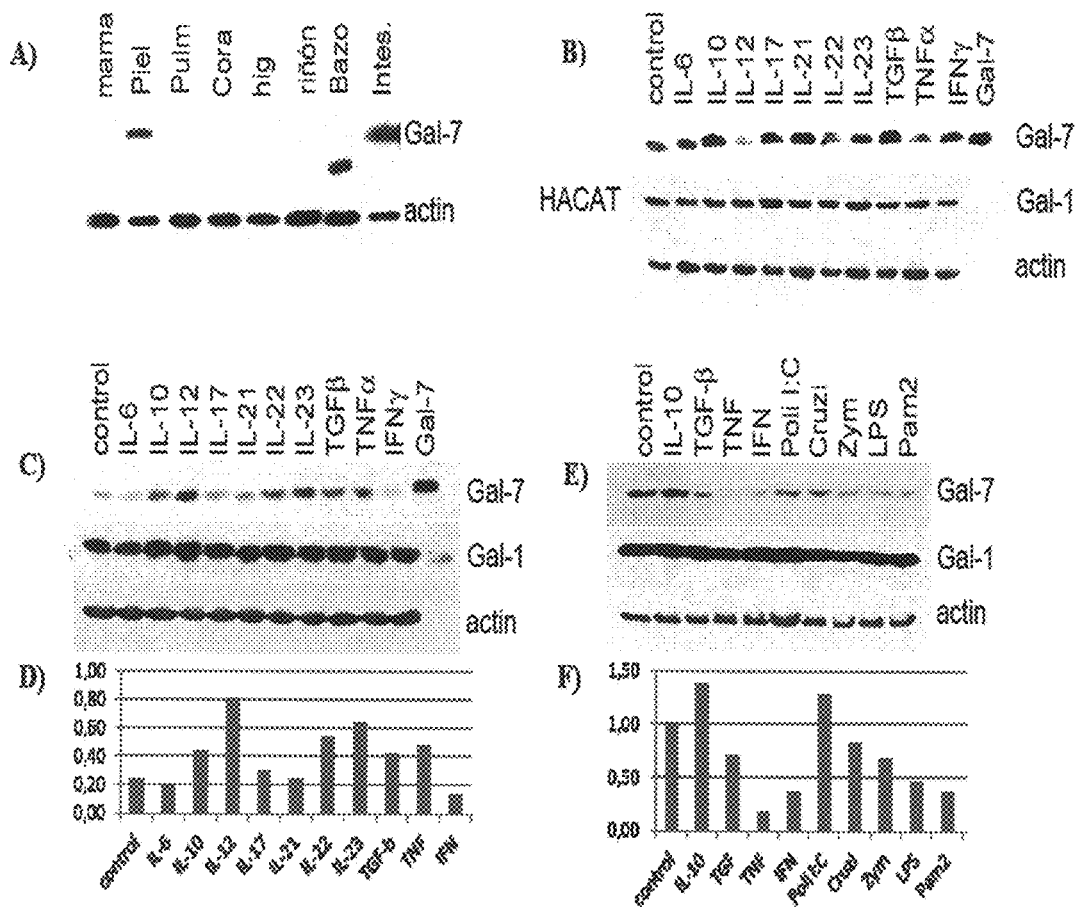
FIGS. 1A-1F Regulation of Gal-7 Expression: 1A) Image of a Western Blot where Gal-7 expression is observed in different tissues; 1B) image of a Western Blot where the differential expression of Gal-7 and Gal-1 in HaCaT cells is observed; 1C) in primary keratinocyte cultures of mice stimulated with different cytokines; and 1D) its quantification; 1E) image of a Western Blot where the differential expression of Gal-7 and Gal-1 in a primary culture of keratinocytes stimulated with different PAMPs; and 1F) its quantification. A representative experiment is shown from a total of 3 with similar results.

When introducing elements of various embodiments, the articles "a," "an," "the" and "said" are intended to mean that there are one or more of the elements. The terms "comprising," "including" and "having" are intended to be inclusive and mean that there may be additional elements other than the listed elements.

References (patent application publications, issued patents, or journal publications) cited in the present disclosure are incorporated by reference herein in their entireties. Also incorporated by reference are the Figures and any polynucleotide and polypeptide sequences that reference an accession number correlating to an entry in a public database, such as those maintained by the Institute for Genomic Research (TIGR) and/or the National Center for Biotechnology Information (NCBI).

The invention provides methods and pharmaceutically acceptable compositions for prevention and treatment, and methods for the manufacture thereof, of epidermal and dermal immune system disorders and inflammation by modulating the galanin-7 (Gal-7) receptor pathway in the skin, such as for example, by administering to an individual in need thereof an effective amount of Gal-7, or a functional fragment of Gal-7, or an agonist or an antagonist thereof.

In certain embodiments the invention provides methods for treating and preventing psoriasis and associated conditions comprising, administering to an individual in need thereof a pharmaceutical composition comprising an effective amount of Gal-7, or a functional fragment of Gal-7, or an agonist of Gal-7, thereby treating the psoriasis and associated conditions. In embodiments, the administration of a pharmaceutical composition comprising an effective amount increases the presence of dermal regulatory T lymphocytes in the patient. In embodiments, the administration of a pharmaceutical composition comprising an effective amount of Gal-7, or a functional fragment of Gal-7, or an agonist of Gal-7, activates Langerhans cells to stimulate T-cell differentiation to regulatory T lymphocytes in the patient.

The invention provides for the treatment and prevention of epidermal and dermal conditions selected from, for example, dermal immunity, dermal inflammation, erythematous plaques, allergic contact dermatitis, parakeratosis, acanthosis, parakeratosis, autoimmune disease and psoriasis.

The invention provides for the methods of treatment and prevention of psoriasis, dermal inflammation, and associated dermal immunity conditions using a pharmaceutical composition comprising an agonist of Gal-7 to stimulate the signaling, expression or distribution of Gal-7 in the individual's skin. Agonists of Gal-7 are known in the art and can be further identified through routine screening of compound libraries.

In certain embodiments the invention provides for the methods of treatment and prevention of psoriasis, dermal inflammation, and associated dermal immunity conditions as described above using a pharmaceutical composition comprising an agent that mimics the interaction between Gal-7 and a natural binding partner of Gal-7. Such agents are known and can be further identified through routine screening of compound libraries.

In certain embodiments the invention provides that Gal-7, or functional fragment of Gal-7, may be naturally occurring or synthetically produced. The Gal-7, or functional fragment of Gal-7, may be a recombinant protein. The recombinantly produced protein may be expressed and purified ex vivo for administration, or be produced in vivo via delivery to the patient of an encoding nucleic acid sequence. The recombinant Gal-7 can be 75%, 80%, 85%, 90%, 95%, 96%, 97%, 98%, 99% or 100% identical to SEQ ID NO:1.

Provided in some embodiments are pharmaceutical compositions, and methods of use thereof, for treating a dermal immune disorder (e.g., psoriasis, inflammation or associated conditions). A pharmaceutical composition of certain embodiments of the present invention can comprise an isolated or partially purified Gal-7 protein, or a functional fragment thereof, suspended in a pharmaceutically acceptable composition comprising demulcent, excipient, astringent, or emollient. In some embodiments, a pharmaceutical composition provided herein comprises a pharmaceutically acceptable carrier for topical administration.

In certain embodiments of the treatment methods described herein, the Gal-7, or functional fragment of Gal-7, may be administered to a subject in a pharmaceutical composition that also comprises pharmaceutically acceptable carriers or vehicles comprising any physiologically acceptable materials, and/or any one or more additives known in the art. In embodiments, carrier and vehicle materials are suitable for topical and transdermal drug administration. Carriers and vehicles useful herein include any such materials known in the art, which are nontoxic and do not interact with other components of the composition in a deleterious manner. For example, solvents, including relatively small amounts of saline or alcohol, may be used to solubilize protein. Other optional additives include opacifiers, antioxidants, fragrance, colorant, gelling agents, thickening agents, stabilizers, surfactants, and the like. Other agents may also be added to the pharmaceutical composition, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. Permeation enhancers and/or irritation-mitigating additives may also be included in the pharmaceutical composition of the present invention.

Modes of administration of the pharmaceutical compositions according to methods provided herein include, but are not limited to, transdermal, parenteral, intradermal, subcutaneous, intramuscular, intravenous, transmucosal, oral, nasal and rectal administration. In various embodiments, the pharmaceutical composition may be administered to an individual, human or animal, in need thereof in the form of, e.g., a cream, a gel, an ointment, an injectable solution, an aerosol, a nasal spray, a suppository, a tablet, or a capsule. The composition may include a nucleic acid that has been inserted into a vector, and the vector administered to the subject in need thereof in a composition by intravenous injection, local injection, or sterotactic injection.

As used herein, "individual" refers to any healthy animal, such as a mammal (e.g., a human) or any animal afflicted with a disease or condition that would benefit from modulation of the Gal-7 pathway. The term "individual" is interchangeable with "subject" or "patient."

The term "pharmaceutically acceptable" means having been approved by a regulatory agency of the Federal or a state government or listed in the U.S. Pharmacopeia or other another generally recognized pharmacopeia for use in animals, and more particularly for use in humans.

As used herein, the term "effective amount" refers to amounts that, when administered to a particular individual in view of the nature and severity of that individual's disease or condition, will have a desired therapeutic effect, e.g., an amount that will cure, prevent, inhibit, or at least partially arrest or relieve a target disease or condition. In certain embodiments, the pharmaceutically effective concentration of Gal-7 protein is in a range of 10-10,000 µg/mL, 50-5,000 µg/mL, or 100-1,000 µg/mL. Dosages will depend upon the severity of the disorder and condition of the individual, and the routine determination at the discretion of a skilled physician.

As used herein, "administering" refers to various means of introducing a pharmaceutically acceptable composition comprising Gal-7 according to the invention, to a cell or tissue, or to a patient. These means are commonly known in the art, include those specifically discussed herein, e.g., transdermal, parenteral, intradermal, subcutaneous, intramuscular, intravenous, transmucosal, oral, nasal and rectal administration.

As used herein, the term "inhibit" includes the decrease, down-regulation, or antagonization, of, e.g., a particular action, function, or interaction. As used herein, the term "promote" includes the increase, up-regulation or agonization, of, e.g., a particular action, function, or interaction. As used herein, the term "modulate" includes up-regulation and down-regulation, e.g., enhancing or inhibiting a response.

The term "dosage unit form" refers to physically discrete units suited as unitary dosages for the subjects to be treated; each unit containing a predetermined quantity of active compound calculated to produce the desired therapeutic effect in association with the required pharmaceutical carrier.

As used herein, the term "T cell" includes CD4+ T cells, CD8+ T cells and NKT cells. The term T cell also includes both T regulatory cells, T helper 1 type T cells, T helper 2 type T cells, T helper 17 type T cells and T helper 22 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the terms "treat" or "treatment" refer to relief from, or alleviation of pathological processes mediated by Gal-7 binding and expression. In the context of the present invention, the terms mean to relieve or alleviate at least one symptom associated with a condition or disease that would benefit from modulation of Gal-7 to effect an immune response, or to slow or reverse the progression of such condition or disease.

As used herein, the term "agonist" refers to a chemical that binds to a receptor and activates the receptor to produce a biological response. Whereas an agonist causes an action, an "antagonist" as used herein refers to a chemical that blocks the action of the agonist, and an inverse agonist causes an action opposite to that of the agonist. In the present invention, Gal-7 is considered an endogenous agonist.

The term "Gal-7" as used herein refers to known Gal-7 sequences, domains, polypeptides, fragments, and variants thereof, as well as gene products of the Gal-7 gene and/or modulators thereof. Specifically, the term Gal-7 refers to native Gal-7 and functional amino acid substitutions, modifications and variants thereof. A functional fragment of Gal-7 exhibits at least 20%, 30%, 40%, 50%, 60%, 70%, 80%, 90%, or 95% of the immune modulating effect of human Gal-7, as measured qualitatively, mechanically, optically, electrically, or by biochemical assay. A functional fragment of a protein comprising amino acid sequences sufficiently homologous to, or derived from, the amino acid sequence of the protein, which includes fewer amino acids than the full length protein, and exhibits at least one activity of the full-length protein. Typically, a biologically active portion comprises a functional domain or motif with at least one activity of the protein. A biologically active portion of a protein can be a polypeptide which is, for example, 10, 25, 50, 75, 100, 125, 135, or more amino acids in length.

Sequences, structures, regions (e.g., the beta-galactosidase binding region), domains (e.g., the galectin domain), and certain biophysical characteristics and functions of Gal-7 protein and genes are well-known and have been described in the art. See, e.g., Madsen et al., Cloning, expression, and chromosome mapping of human galectin-7, J. Biol. Chem. 270:5823-5829 (1995); Leonidas et al., Structural basis for the recognition of carbohydrates by human galectin-7, Biochemistry 37:13930-13940 (1998). Therefore, the selection of a functional fragment of Gal-7 is a routine matter. The native human Gal-7 amino acid sequence is provided below.

```
Protein Sequence of Native Human Gal-7 (136 aa)
                                       (SEQ ID NO: 1)
MSNVPHKSSL PEGIRPGTVL RIRGLVPPNA SRFHVNLLCG

EEQGSDAALH FNPRLDTSEV VFNSKEQGSW GREERGPGVP

FQRGQPFEVL IIASDDGFKA VVGDAQYHHF RHRLPLARVR

LVEVGGDVQL DSVRIF
```

As used herein, the term "homologous" refers to Gal-7 nucleotide, protein or polypeptide sequence similarity between two regions of the same nucleic acid or amino acid strand or between regions of two different nucleic acid or amino acid strands. When a nucleotide or amino acid residue position in both regions is occupied by the same nucleotide or amino acid residue, then the regions are homologous at that position. A first region is homologous to a second region if at least one nucleotide or amino acid residue position of each region is occupied by the same residue. Homology between two regions is expressed in terms of the proportion of nucleotide or amino acid residue positions of the two regions that are occupied by the same nucleotide or amino acid residue. For nucleic acids and polypeptides, the term "substantial homology" indicates that two nucleic acids or amino acids, or designated sequences thereof, when optimally aligned and compared, are identical, with appropriate nucleotide or amino acid insertions or deletions, in at least about 80% of the nucleotides or polypeptides, usually at least about 81%, 82%, 83%, 84%, 85%, 86%, 87%, 88%, 89%, 90%, 91%, 92%, 93%, 94%, 95%, 96%, or more of the nucleotides and polypeptides, and more preferably at least about 97%, 98%, 99% or more of the nucleotides and polypeptides. Alternatively, substantial homology exists when the segments will hybridize under selectively stringent hybridization conditions, to the complement of the strand.

The "percent identity" between two sequences is a function of the number of identical positions shared by the sequences (i.e., % identity=# of identical positions/total # of positions×100), taking into account the number of gaps and the length of each gap that needs to be introduced for optimal alignment of the two sequences. The comparison of sequences and determination of percent identity between two sequences can be accomplished using a mathematical algorithm.

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Methods for isolation, purification, and recombinant expression of a protein are well known in the art. In certain embodiments, the method starts with cloning and isolating mRNA and cDNA encoding Gal-7 proteins or isoforms using standard molecular biology techniques, such as PCR or RT-PCR. The isolated cDNA encoding the Gal-7 protein or isoform is then cloned into an expression vector, and further transformed and expressed in a host cell for producing recombinant Gal-7 protein.

As used herein, the term "nucleic acid" is intended to include DNA molecules and RNA molecules. A nucleic acid molecule may be single-stranded or double-stranded, but preferably is double-stranded DNA. As used herein, the term nucleic acid molecule is intended to include DNA molecules (e.g., cDNA or genomic DNA) and RNA molecules (e.g., mRNA) and analogs of the DNA or RNA generated using nucleotide analogs.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. In some embodiments an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, an "isolated" nucleic acid molecule, such as a cDNA molecule, can be substantially free of other cellular material, or culture medium, when produced by recombinant techniques, or substantially free of chemical precursors or other chemicals when chemically synthesized. In embodiments, a nucleic acid molecule can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences can be prepared by standard synthetic techniques, e.g., using an automated DNA synthesizer.

In certain embodiments, an isolated nucleic acid homolog encoding the Gal-7 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such Gal-7 protein (e.g., SEQ ID NO:1).

Furthermore, the Gal-7 protein used herein includes Gal-7 protein encoded by a polynucleotide that hybridizes to the polynucleotide encoding Gal-7 protein under stringent conditions. As used herein, "hybridization" includes a reaction in which one or more polynucleotides react to form a complex that is stabilized via hydrogen bonding between the bases of the nucleotide residues. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding Gal-7 protein described herein. As used herein, the term "stringent conditions" refers to hybridization overnight at 60° C. in 10× Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10× Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are well known in the art. Accordingly, the Gal-7 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human Gal-7 protein (e.g., SEQ ID NO:1) or a specific isoform or homolog thereof.

Moreover, the Gal-7 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of Gal-7 protein with other Gal-7 protein isoforms.

As used herein, the term "vector" refers to a nucleic acid capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. The terms "plasmid" and "vector" may be used interchangeably, as the plasmid is the most commonly used form of a vector. However, the disclosure is intended to also include other forms of expression vectors that serve similar functions, such as, e.g., as viral vectors.

It should be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

This Example focuses on elucidating the immunological functions of Gal-7, a protein that is preferentially expressed in keratinocytes, and on identifying an immunological circuit responsible for limiting the skin's inflammatory response. Briefly, keratinocytes exposed to different inflammatory stimuli increased the expression of Gal-7, which binds to specific glycans in Langerhans cells (LCs), promoting a tolerogenic phenotype in these cells (producer of IL-10, IL-27, and TGF-β). Tolerogenic LCs are capable of polarizing T response to a regulatory FoxP3+ profile. Using different experimental models and mice strain (transgenic or Gal-7-deficient mice specific for this lectin), this example demonstrates that this regulatory circuit is responsible for controlling in vivo the skin's inflammatory response.

At present, psoriasis is considered an autoimmune disease, and even though the initial circumstances that trigger the onset of this pathology are not quite clear, its progression, both in the initial acute inflammatory stage and then in the subsequent chronic stage, has been described (Martin et al., 2013). Among all the cells that characterize the erythematous plaque infiltrate, Th1 lymphocytes are considered responsible for the initial inflammatory process, whereas Th17 lymphocytes (and also Th22 in humans) may be responsible for maintaining the inflammation over time. Th17 and Th22 also promote proliferation of keratinocytes by means of IL-22, thus determining the formation of erythematous plaques and acanthosis.

The example of the invention analyzes the different components that are a part of the proposed immunological circuit. The invention identifies the Gal-7 axis and its specific glycans as biological mediators that link keratinocytes, LCs, and Treg lymphocytes during the resolution of the inflammatory response. In this way, Gal-7 derived from keratinocytes confers to LCs a tolerogenic phenotype capable of polarizing in the lymph nodes the response of the T lymphocytes to a regulatory profile responsible, in turn, for suppressing local inflammatory reactions in the skin. Based on an interdisciplinary approach and both in vitro and in vivo assays, the invention demonstrates for the first time the role that Gal-7 plays in the physiology of the LCs and its key role in epidermal homeostasis.

Evaluation of the profile of Gal-7 expression was the first objective. The invention provides that in addition to a high expression in the epidermis, Gal-7 is also expressed in other tissues, such as the intestinal epithelium and the spleen cells (FIG. 1).

Along with these tissues, previous studies have demonstrated that the ovary epithelium, the mammary duct glands, the trachea epithelium, and the cornea epithelium all express this lectin too. In other words, not only the stratified epithelia can express this protein. In particular, it has been proven that the Gal-7 expressed by the cornea epithelium is capable of promoting re-epithelialization of the lesions by increasing cell migration. Therefore, treatment with rGal7 may promote re-epithelialization, without promoting cell proliferation. This last point is quite favorable as compared to treatments with different growth factors, which have an unwanted side effect in relation to the possible neoplastic transformation of the tissues where it is used (Cao et al., 2002; Cao et al., 2003).

In the second place, this example of the invention evaluates the regulation of Gal-7 expression in primary cultures of murine keratinocytes and in an immortalized line of human keratinocytes. The results show that this lectin can be regulated by different cytokines and TLR agonists (FIG. 10). These cytokines can be secreted by the keratinocytes themselves or by leukocytes, in basal or inflammatory conditions. Even though Gal-7 synthesis in the differentiated keratinocytes is constitutive, it may also be regulated by specific stimuli, either external (pathogens, abrasions, etc.) or internal (autoimmunity) stimuli. This evidence, in the first place, indicates that Gal-7 plays a key role in the physiology of the skin's immunological system, in particular, regarding LCs, a type of DCs that are in intimate contact with keratinocytes.

In this example of the invention, LCs were also differentiated from bone marrow precursors and to obtain protein extracts to analyze by Western Blot. This assay enabled corroboration not only that this cell type does not express the lectin under study, but also that Gal-7 is capable of binding to LC glycoproteins. The capacity of Gal-7 to interact with glycans of LCs prompted study of the molecular mechanism responsible for such interactions.

Thus, this example of the invention characterizes the profile of glycans decorating LC membrane proteins, at basal stages (control) or subsequent to activation with a TLR agonist (activated with poly(I:C)). The incorporation of saccharide residues to glycoproteins consists in one of the most common post-translational modifications of cells induced by internal or microenvironmental stimuli. As described above, there are multiple pathways by which modifications are regulated. The time or space constraints of the glycosyltransferase substrates and modifications in the expression pattern of these enzymes, or in the chaperones that ensure proper folding and subcellular distribution of the glycosytransferases, are just some of the classic examples of the remarkable regulation of cellular glycome. Once the glycoproteins are in the membrane, however, it is highly unlikely that they will undergo modifications.

The invention demonstrates, through in vitro assays, that LCs modify their glycophenotype upon activation. These changes in the structure of glycans decorating the glycoproteins of LCs consisted in an increase in N-glycan complexes, i.e., branching that basally was biantennary is transformed into tri- or tetra-antennary glycans when LCs are activated. In turn, this branching promotes the elongation of the chains, increasing the number of LacNac repeat units and, as a result, the number of sites available for Gal-7 binding. Subsequently, the binding capacity of Gal-7 to activated or unstimulated LCs was evaluated and observed to increase Gal-7 binding to the glycoproteins of activated LCs.

Simultaneously with the increasing branching and elongation of the glycan chains, sialic acid residue in $\alpha 2,6$ position was increased. This modification, which typically affects Gal-1 binding to its specific receptors, does not affect Gal-7 binding to LC glycoproteins. This change or switch in the glycan structure of Langerhans cells when they are activated suggested that Gal-7, and not Gal-1, might be involved in the physiology of LCs in response to specific stimuli.

LCs activated in the presence of Gal-7 induce differentiation of T cells to a regulatory profile. Based on Gal-7 binding to LCs, the impact of this lectin on the tolerogenic potency of these cells and their capacity to promote a regulatory response was studied. Even though lectins do not have a unique characteristic receptor due to their affinity to glycans present in lipids or proteins, binding to glycosylated receptors can activate different signaling pathways in a non-canonical manner as recently demonstrated (Croci et al., 2014). This capacity to bind and activate glycoreceptors is due in part to the fact that galectins can oligomerize (or dimerize as in the case of Gal-7) and form "lattices" or rearrangements of glycosylated membrane receptors, activating signals to the interior of the cell; as a result, galectins can execute specific biological response programs.

This example of the invention showed that LCs differentiated in vitro and incubated with Gal-7 prior to their activation secrete, dependent on concentration of the lectin, higher concentrations of anti-inflammatory cytokines such as TGF-$\beta$1, IL-10, and IL-27 in comparison with LCs activated in the absence of this lectin. On the other hand, LCs activated in the presence of rGal7 evidenced greater capacity to suppress spleen cell proliferation, whereas LCs pre-incubated without rGal-7 promote predominantly immunogenic responses.

Figure 6:
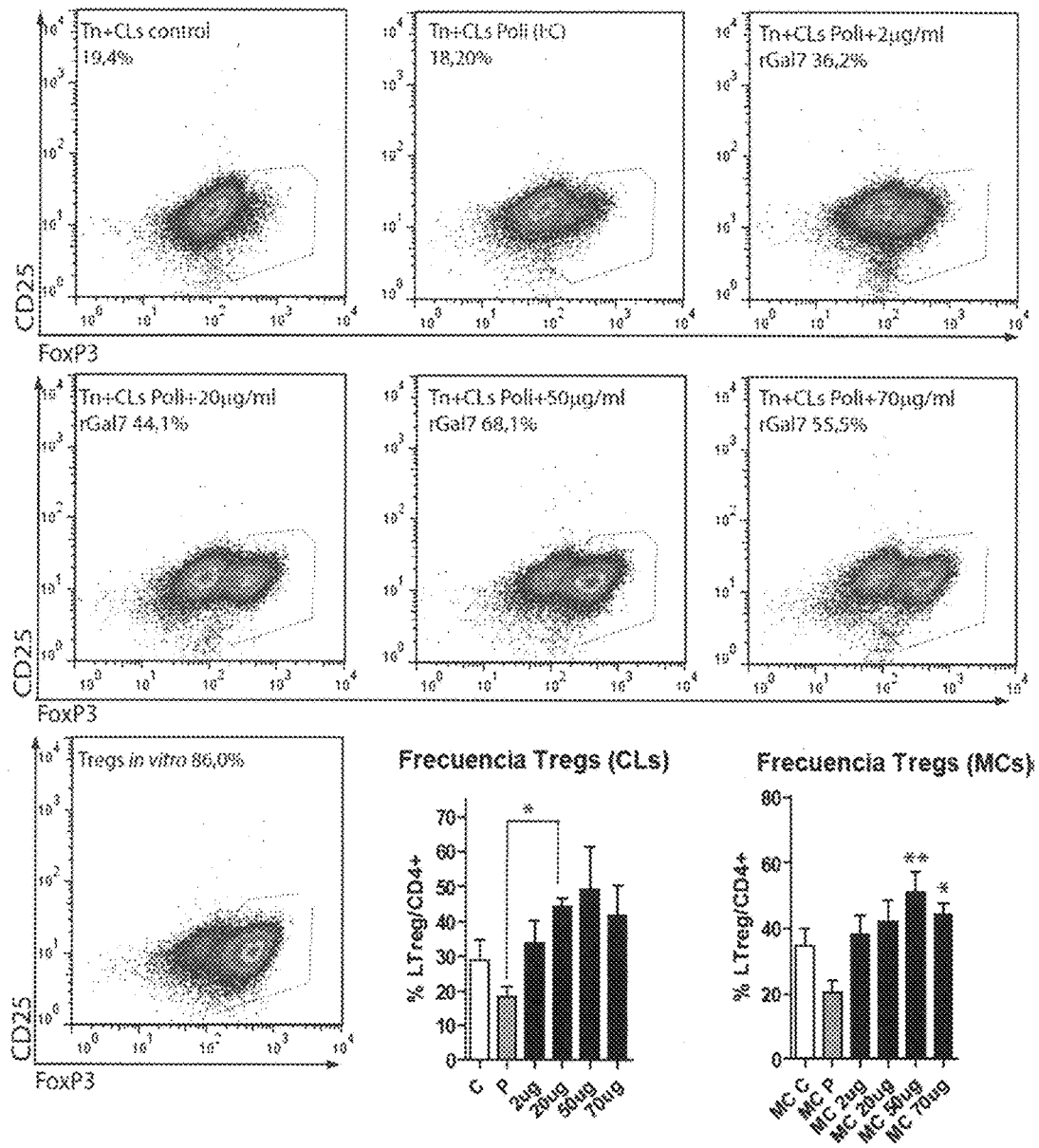
FIG. 6 T cell differentiation by co-cultures with LCs pre-incubated with different concentrations of rGal-7 and with conditioned media from activated LCs. Dot plot of cell populations assayed by cytometry, where Foxp3+ Treg lymphocytes are observed. T lymphocyte differentiation to Treg profile increases dependent on concentration of rGal-7 in the culture medium of LCs activated with poly(I:C) (*$p<0.05$; **$p<0.001$).

Subsequently, to evaluate the differential profile of T cells induced by LCs, the example co-cultivated activated-LCs pre-incubated with rGal-7 and purified naïve T cells. In addition, the example differentiated naïve T lymphocytes with conditioned media from activated-LCs. In both cases, the example corroborated that growing concentrations of rGal-7 during LC activation promote T differentiation to a Treg profile, disfavoring its differentiation toward Th1 or Th17 profiles (FIGS. 6 and 7).

In particular, differentiation was more efficient when T cells were cultured in contact and not with conditioned media of LCs, pointing to the importance of cell-to-cell contact in this biological effect. It is important to note that naïve T lymphocytes cultured only with rGal-7 showed no differences in the proportion of Tregs (results not shown). Therefore, the LCs themselves and the cytokines that they secreted induce differentiation of the naive T cells toward a Treg profile and do not represent a direct effect of Gal-7.

Among the cytokines secreted by the LCs, the relevance of TGF-β1 in the T differentiation process due to its abundance was evaluated. Therefore, following through with a scheme identical to the one described above, the example supplemented the conditional medium with a TGF-β1 blocking antibody in the LC-naïve T co-culture. Blocking performed by this antibody produced a slight decrease in the percentage of differentiated Tregs (results not shown).

Lastly, the example corroborated the capacity of these T cells differentiated in the co-culture to suppress spleen cell proliferation in an MLR assay. In these assays, Tregs differentiated in cultures with LCs and not with their conditioned medium reduced spleen cell proliferation, demonstrating that LCs exposed to Gal-7 not only confer a regulatory phenotype to T cells through characteristic differentiation markers, but they are also capable of amplifying the immunosuppressor potency (FIG. 7).

In this context, through a series of in vitro assays, the example was able to recreate the components of this possible immunological circuit. Different concentrations of Gal-7 secreted by keratinocytes may have an impact on LC activity, whereby LCs might be capable of differentiating Treg cells to an immunosuppressor phenotype. The example demonstrated that the presence of Gal-7 in the LC activation microenvironment determines its capability to induce a regulatory profile in T cells; this regulatory profile contributes to maintaining the homeostasis of the immune system, limiting the inflammatory response of Th1, Th17, and Th22 in the skin. These T lymphocyte populations, plus the CD8+ and polymorphonuclear cells, are responsible for generating and maintaining cutaneous inflammation in different pathologies. As a result, Gal-7 appears to contribute to inducing Treg differentiation, blocking the activity of the effector T cells involved in perpetuating inflammatory response. These results highlight evidence on the role of Gal-7, a lectin expressed in a regulated manner by keratinocytes, as a new linker between glycobiology and the immune system in the skin.

Gal-7 Modulates the Resolution of Inflammatory Response in Two Cutaneous Inflammation Models. Psoriasis and Contact Irritation Psoriasis and ICD are two pathologies characterized by cutaneous inflammation; in these pathologies, Th1, Th17, and Th22 cells are the main effector lymphoid cells of the inflammation.

On the other hand, the role of LCs in these pathologies is unclear. During ACD, the function of these antigen-presenting cells residing in the skin is controversial, given that no strict consensus has been achieved to date on their immunogenic or regulatory function. In this sense, there are different murine models where all the Langerin+(both dermal and epidermal) cells can be depleted by administering diphtheria toxin in genetically modified mice that have the toxin receptor inserted under a Langerin promoter. Using these mice, a time window may be created where the dermis is re-populated by Langerin+ DCs (dDCs, 3 days), but not the epidermis (LCs, 2 weeks). Various studies have been published using these murine models, whereby it is demonstrated that the DCs involved in the initial sensitization phase are dDCs and not LCs (Kissenpfenning et al., 2005; Bursch et al., 2007; Wang et al., 2008). However, other groups have observed, with similar assays, that LCs can act in a compensatory mechanism in mice specifically depleted of Langerin+ dDCs that develop a normal CHS phenotype (Honda et al., 2010; Noordegraaf et al., 2010; Edelson et al., 2010). In turn, the regulatory role of LCs has also been proposed. Using the same animal models, other research groups have demonstrated an exacerbated CHS phenotype complicating ever more our knowledge of the true role of LCs (Kaplan et al., 2005; Igyarto et al., 2009). Similarly, this controversy also is present in pathologies such as psoriasis and ICD.

The specific role of each one of the DC subtypes residing in the skin has yet to be unraveled. Nevertheless, based on the in vitro and in vivo assays already performed, the example observed a higher proportion of Treg cells in draining lymph nodes of Gal-7 Tg mice, compared with WT and Gal-7-deficient mice. This greater number of Treg cells suggests a tolerogenic response, which appears to contribute to the resolution of inflammation in a more efficient fashion in these animals, compared with WT mice and especially Lgals7$^{-/-}$ (KO) mice. On the other hand, the presence of a higher infiltrate of CD4+T lymphocyte, NK cells, and macrophages was observed in skin biopsies of KO mice, a fact that coincides with previous macroscopic observations.

Gal-7 deficient mice, throughout the two treatments, exhibited unique characteristics that suggest a more severe inflammatory process. These KO animals showed greater rubor, higher temperatures, and larger erythematous plaques in the psoriasis model; whereas in ICD, these mice exhibited greater rubor and thickness of the treated ear. In the psoriasis model, the re-stimulated draining lymph nodes cells showed higher secretion of IFN-γ in KO mice compared with Tg mice, as well as a lower percentage of Tregs. Therefore, the example provides that the presence of Gal-7 during LC activation induces a higher percentage of Tregs; Tregs are responsible for suppressing Th1 lymphocytes secretors of IFN-γ, thus resolving in part the skin's inflammatory process. These results in Tg and KO mice models agree on the leading role that Gal-7 plays in the regulation of cutaneous immunological homeostasis.

Gal-7 contributes to the skin's immunological tolerance, thus inducing the resolution of the inflammatory foci in illnesses such as psoriasis and ICD. Based on preliminary results, the application of rGal7 contributes to the resolution of the inflammatory process in both lectin-deficient mice as well as in WT mice. Based on these results, it was reported in 2009 that the active form of vitamin D (1α,25(OH)2-vitamin D3) induced by UVB lighting, promotes tolerance in the affected area of the epidermis (Ghoreishi et al., 2009). Ghoreishi's work describes how UV lighting acts as a stimulus on the keratinocytes to have them secrete vitamin D which, in turn, induces the autocrine expression of RANKL (receptor activator of NF-κB). These two molecules promote differentiation of naïve T lymphocytes to a regulatory phenotype.

However, in addition to these two models, it is known that UV irradiation on the skin induces p53 expression, a transcription factor that regulates positively the Gal-7 gene. As a result, the mechanism proposed by our group may work in a complementary mechanism to the one described by Ghoreishi, determining immunoregulation of the inflammatory process. In this context, Gal-7 may be involved in the resolution of inflammatory foci, generating a tolerogenic microenvironment.

This effect may be performed indirectly by differentiated Treg cells in draining lymph nodes through immunological synapses between a naïve T lymphocyte and LCs. In this regard, the circuit described in this study may act positively in inflammatory pathologies, and negatively in the presence of neoplastic transformations of the skin. In such cases, Gal-7 may contribute to the development of a tolerogenic microenvironment, favorable to the development of tumors. In fact, it has been recorded that in melanomas, a higher expression of Gal-7 is positively correlated to lower sensitivity to apoptosis (Biron-pain et al., 2013). Carcinogenesis assays have commenced to evaluate this hypothesis.

Lastly, and to conclude the work performed in this example, it was inferred that there is an immunological circuit that links keratinocytes, LCs, and Tregs through the Gal-7-glycan axis. Keratinocytes are not passive cells that protect the body from desiccation and pathogenic colonization. They respond to stimuli, both external as well as internal, by secreting cytokines and lectins. These lectins, in particular Gal-7, is capable of modulating the physiology of the immune system cells residing in the skin. Gal-7 is a lectin preferentially expressed in keratinocytes, whose participation in the skin's immunological circuit was rather unclear. Gal-7 binds to LCs (DCs residing in the epidermis) through glycans in proteins of the cell membrane. The interaction between the lectin and the LCs is greater when these cells are activated (branching and the elongation of N-glycan chains increases). Once activated and bound to Gal-7, LCs diminish the expression of E-cadherin, which kept them bound to keratinocytes, and migrate through the lymphatic vessels, maturing along the way. Upon reaching a draining lymph nodes, LCs interact with T lymphocytes, whose TCR recognizes the antigen/MHC II complex.

These T lymphocytes are activated, and in response to the cytokines secreted by the mature LCs, they become differentiated. Immunologic synapses are capable of directing the T lymphocytes to inflammatory profiles Th1, Th17 and Th22, or tolerogenic response characterized by T differentiation to the Treg profile (CD4+, CD25+, FoxP3+). Differentiation according to any of the two profiles depends on the cytokines secreted by the LCs and the latter, in turn, depend on the cytokine microenvironment where they were activated.

This suggests that the interaction between Gal-7 and the glycoproteins of LCs may substantially modify the physiology of these cells, thus contributing to their differentiation to a profile that regulates negatively the inflammatory immune response.

Finally, the results of the psoriasis and ICD models indicate that the higher concentration of Gal-7 present in the epidermis of Tg mice contributes to maintaining a homeostasis state that counteracts against the inflammation generated by Imiquimod and TPA. Therefore, the use of Gal-7 as a possible therapeutic agent, by topical application to patients exhibiting persistent skin irritations, is a new field of research. Topical treatment with rGal-7 can be used as an alternative or complementary therapy to the treatments currently employed (blocking of TNF-α, blocking of IL-21, IL23 and IL-17, application of calcipotriol, etc.). In this context, this example describes an immunological circuit in the skin, mediated by keratinocytes, LCs, and Treg cells, which involves fundamental components such as Gal-7, specific glycans, and anti-inflammatory cytokines.

Materials & Methods

Breeding of Mice

C57BL/6 strain WT mice obtained from the Universidad Nacional de la Plata (UNLP), as well as Gal-7-deficient mice (Lgals7$^{-/-}$) and transgenic for Gal-7 (Tg 34 and 46) mice obtained from the laboratory of Dr. Francoise Poirier at the Institut Jacques Monod (Paris, France) were bred and maintained at the Vivarium of the Instituto de Biologia y Medicina Experimental (IBYME). In all the experiments, 8- to 12-week-old mice were used. The experimental protocols were approved by the IBYME's Institutional Ethics Counsel.

Tissue Processing

Murine ears were cut and separated into their dorsal and ventral sections. They were placed in an enzymatic solution of dispase II (10 mg/ml; Roche) for 2 hours to separate the dermis from the epidermis. Once the two layers were separated, the epidermis was placed in TrypLE Express (GIBCO) for 20 min. and cut into 1 cm$^2$ pieces to facilitate disaggregation. Cell suspension was filtered with a 100 μm mesh and centrifuged; the cell pellet was resuspended in a buffer or culture medium to obtain a unicellular suspension. Spleen cells were obtained by mechanical disruption of the spleen and then filtered using a 100 μm mesh; a 10-minute spin at 300 g was performed and the cell pellet resuspended in a red blood cell lysis buffer (NH4Cl 154 mM, KHCO3 1 mM, EDTA 0.1 mM) for 5 minutes. The reaction was interrupted by diluting with physiological solution, centrifuged for 10 minutes at 300 g and the cell pellet was resuspended in a buffer or culture medium. Processing of lymph nodes to obtain splenocytes was similar to the procedure described above for the spleen, except that the step with the red blood cell lysis buffer was not performed.

Keratinocyte Cultures

Keratinocytes from C57BL/6j WT mice and immortal human keratinocytes (HaCaT) were cultivated in DMEM (GIBCO®) supplemented with 10% (v/v) fetal calf serum (GIBCO®). These cells were seeded on flat-bottom, 24-well plates for adherent cells (GBO). Once adequate cell density was achieved (approx. an 80% confluence), the keratinocytes from the primary culture and the HaCaT cells were maintained in DMEM+1% FBS for 24 hours. Subsequently, they were incubated with IFN-γ (50 ng/ml), TNF-α (20 ng/ml), IL-1β (1 ng/ml), IL-6 (2 ng/ml), IL-10 (50 ng/ml), IL-17 (5 ng/ml), IL-21, IL-22, IL-23, TGF-β1 (5 ng/ml) and Toll agonists, LPS (TLR4), Pam2CSK4 (TLR2,6), Pam3CSK4 (TLR2,1), peptidoglycan (PGN; TLR2), poly(I:C) (TLR3), zymosan (TLR2), P. acnes (TLR2,4), flagellin (TLR5) for 24 hours. Once the stipulated time is over, the culture medium was collected for ELISA and the cells were subjected to cellular lysis for Western blot assays.

ELISA

Conditioned keratinocyte media, or cell differentiation or activation in culture (LCs, T Lymphocytes, draining lymph nodes cells), were obtained by centrifugation at 2000 rpm for 5 min. and the supernatant collected. Analyses of these conditioned media were performed to determine the concentration of TGF-β1 (BD), IL-10 (BD), IL-27 (BD) in an LC supernatant; IFN-γ (R&D), IL-17 (BD) and IL-22 (BD)

in a T lymphocyte supernatant culture; Gal-7 (R&D) in cultured keratinocyte supernatants according to the manufacturer's instructions.

Obtaining Protein Extracts from Tissues and Cell in Culture

Different tissues were cut into approximately 100 mg sections and homogenized with an Ultra-Turrax in the presence of a lysis buffer (Tris-HCl pH 7.5 50 mM, NaCl 150 mM, EDTA 10 mM, NP40 1%). The cultured or suspended cells were homogenized in a lysis buffer (Tris-HCl pH 7.5 50 mM, NaCl 150 mM, EDTA 10 mM, NP40 1%), along with a commercial protease inhibitor (SIGMA). In all cases, lysates were kept for 1 hour in ice, after which they were centrifuged at 12,000 rpm in a microcentrifuge refrigerated at 4° C. The extract, a supernatant from centrifugation, was stored in a freezer at −70° C. until further use. Protein concentration was quantified by Micro BCA™, a commercial assay kit, with a standard BSA curve according to the manufacturer's instructions (Thermo Scientific). Readings were taken at 2\, =595 nm in a Multiskan™ Microplate Spectrophotometer (Thermo Electron Corporation).

Western Blot

The total protein extracts obtained from cellular lysis were run in denaturing polyacrylamide gels (SDS-PAGE). To accomplish this, 20 µg of protein were seeded for a sample previously denatured in a 2× sample buffer (BIO-RAD) for 3 min at 100° C. The attempt was made to have equal seed volumes for all samples. A 10 kDa-170 kDa (Fermentas) molecular weight marker was used.

Resolution gel at 12%: Acrylamide 30%/N'N'-Bis-Acrylamide 0.8% 3.4 ml, buffer resolution at 2.5 ml, 4 ml of water, SDS 10% 100 µl, TEMED 10 µl, APS 10% 70 µl.

Concentration Gel: Acrylamide 30%/N'N'-Bis-Acrylamide 0.8% 650 µl, concentration buffer (0.5 M Tris, SDS 0.4% p/v at pH=6.8) 1.25 ml, 3 ml of water, SDS 10% p/v 50 µl, 10 µl TEMED, APS 10% p/v 50 µl.

The electrophoretic run was performed at 150 constant volts for 60 to 90 min in a running buffer (25 mM Tris, 195 mM glycine, 0.1% SDS). The samples were transferred to a nitrocellulose membrane (GE Healthcare) in a transfer buffer (25 mM Tris, 195 mM glycine, 20% methanol) at 250 mA constant for 60 to 90 min. Once the transfer concluded, the membranes were washed in TBS Tween (150 mM NaCl, 50 mM Tris at a 7.4 pH, Tween 20 0.1% v/v) and were stored in the refrigerator or used immediately. For immunoblotting, the membranes were treated to the appropriate antibodies as detailed below (Table 1).

TABLE 1

| Antibody | Origin of the Species | Blocking | Primary Antibody | Secondary Antibody |
|---|---|---|---|---|
| Anti-Gal-1 (Ilaregui et al., 2009) | Rabbit; Human/Mouse | 5% skimmed milk | TBSt, 2 hr TA | TBSt, 1 hr TA |
| Anti-β-actin (Sta. Cruz, sc-1616-R) | Rabbit; Human/Mouse | 5% skimmed milk | TBSt, 2 hr TA | TBSt, 1 hr TA |
| Anti-Gal-7 (Polyclonal; Abcam ab10482) | Rabbit; Human/Mouse | 5% skimmed milk | TBSt, 2 hr TA | TBSt, 1 hr TA |

Anti-mouse or anti-rabbit secondary antibodies (both from Vector) were used attached to the HRP enzyme and incubated for 1 hour at TA in TBS Tween 0.1%. A commercial chemiluminescence reagent (Millipore) was used and developed in a darkroom with X-ray plates (Kodak) or in G-Box.

Differentiation and Activation of Langerhans Cells

Dendritic cells were differentiated from bone marrow precursor cells of C57BL/6j WT mice as discussed by Ilarregui et al., (2009). In short, bone marrow precursor cells were obtained from the femur and tibia of mice of the strains mentioned above and cultured in a RPMI (GIBCO) culture medium supplemented with 10% v/v FBS, 10% v/v GM-CSF (obtained from the supernatant of J588 cells), 10 ng/ml of TNF-α (R&D), 20 ng/ml of TGF-β1 (20 ng/ml), 1 mM of HEPES (GIBCO) and 50 µm β-mercaptoethanol (GIBCO) until their differentiation to LCs.

Once differentiation has terminated (approximately 7 days), the LCs were centrifuged, resuspended in RPMI+10% v/v FBS and later subjected to various treatments:

Control LCs, unstimulated, incubated only in a culture medium.

Activated LCs, incubated with 10 m/ml of poly(I:C).

LCs pre-incubated for 30 min with different concentrations of rGal-7 (at 2 µg/ml, 20 µg/ml, 50 µg/ml, and 70 µg/ml), and later activated with 10 µg/ml of poly(I:C).

At twenty-four hours post-activation, these LCs were centrifuged at 1000 rpm in a microcentrifuge refrigerated at 4° C. and the conditioned medium was collected to analyze TGF-131 and IL-10 cytokines by ELISA. In turn, the LCs were stained with specific antibodies to evaluate the percentage of differentiation from bone marrow precursors and then evaluated their glycophenotype. Lastly, the conditioned media from LC activation were used in mixed cultures to evaluate virgin T cell differentiation to regulatory or effector phenotypes.

T Cell Differentiation

CD4+ T lymphocytes were purified from spleen cells by negative selection with magnetic beads conjugated to antibodies (Dynal Mouse CD4 Negative Isolation Kit, Invitrogen) and resuspended in a Miltenyi buffer (PBS, BSA 0.5% EDTA 2 mM). The protocol was performed according to the manufacturer's instructions. Naïve T cells were purified from this CD4+ population by sorting, as described. In short, lymphocytes were incubated in the dark at 4° C. with anti-CD4 APC antibodies (clone GK1.5; eBioscience): 1/200 stock dilution (0.2 mg/ml) and anti-CD62L PE antibodies (clone MEL-14; BD Pharmigen): 1/200 stock dilution (0.2 mg/ml). By using a BD FACS Aria II flow cytometer, naïve T cells (double positive) were separated and collected in a test tube containing RPMI+10% v/v FBS.

Subsequently, the cells were centrifuged for 10 min at 2000 rpm and resuspended in RPMI supplemented with 10% v/v FBS, 2 ng/ml of TGF-β1 (concentration supra-basal to differentiation of regulatory T cell), and 100 UI/ml of rIL-2 (R&D). The cells were seeded in U-bottom, 96-well plates, at a rate of 200,000 cells per well, which were then incubated under the following conditions:

Cocultures with 50,000 LCs under control conditions, activated with poly(I:C), pre-incubated with different concentrations of rGal-7, and later activated with poly (I:C);

Incubated with a 1/50 dilution of LC-activated conditioned media under the three conditions mentioned above;

Incubated with 5 ng/ml de TGF-β1 (in vitro differentiation of regulatory T cells, positive Treg control);

Unstimulated, in order to evaluate the percentage of naïve T cells capable of differentiating spontaneously in cultures (negative Treg control).

The in vitro differentiated cells under the conditions mentioned above were incubated in each well at a final volume of 200 μl for 3 days at 37° C. Finally, one part of these differentiated T cells was used subsequently in a mixed lymphocyte culture and the other part was stained to evaluate the percentage of differentiated Treg cells. The conditioned media were collected for the subsequent cytokine analysis by ELISA (IFN-γ, IL-17, and IL-22).

Mixed Lymphocyte Culture

Spleen cells from C57BL/6j strain mice were cocultured with irradiated spleen cells from BALB/c strain mice (non-proliferative) and co-incubated with:

Activated LCs (control; activated with poly(I:C); preincubated with different concentrations of rGal-7, and then activated with poly(I:C)).

T cells from the differentiation assay described above.

Dilutions at 1/50 of the conditioned differentiation media from the naïve T cells.

The cells were seeded in U-bottom, 96-well plates pre-incubated with anti-CD3 (eBioscience) at a concentration of 5 μg/ml in 40 μl of PBS 1× in a humid chamber for 2 hours at 37° C.

The cells were cultured in RPMI+10% v/v FBS supplemented with 1 μg/ml of anti-CD28 (eBioscience) at a final volume of 200 μl for 3 days at 37° C. Cellular proliferation was determined upon the addition of tritiated thymidine [$^3$H]-thymidine in day 3 of culture.

Cellular Proliferation

At the end of the proliferation assays, the cells were incubated with 1 μCi of [$^3$H]-thymidine (Perkin Elmer) per well. After 16 hours, the cells were harvested using a Micro96 Harvester (Molecular Devices). Proliferation was quantified by counts per minute (cpm) in a β-radiation counter.

Flow Cytometry

Regulatory T Cell Staining:

Cells from the epidermis, lymph nodes, spleen, or cell culture were resuspended in a 30 μl flow cytometry buffer (FACS Staining Buffer by eBioscience); the cells were marked with specific conjugated antibodies as follows:

Treg Cells: CD4-FITC (clone RM4-5; eBioscience) 0.25 μg/tube;

CD25-PE (clone PC61.5; BDPharmigen): 0.2 μg/tube;

Foxp3-APC (clone FJK-16s; eBioscience): 1 μg/tube.

In the first place, anti-CD4-FITC and anti-CD25-PE (or anti-CD4-APC and anti-CD44-FITC) surface antibodies were used for staining in FACS Staining Buffer for 30 to 60 min at 4° C. Subsequently, Fixation/Permeabilization Buffer (eBioscience) was used for fixation and permeabilization. The cells were resuspended in this buffer and kept for 18 hours in a humid chamber at 4° C. Then the intracytoplasmic marker FOXP3 was used, incubating the cells for 1 hour at 4° C. with anti-Foxp3-APC (or conjugated with PE) in a permeabilization buffer (eBioscience). Finally, the cells were washed and resuspended in 200 μl of paraformaldehyde at 1% v/v until analyzed for flow cytometry in a BD FACS Canto flow cytometer.

Characterization of Glycophenotype of Murine LCs:

Two strategies were used to evaluate the glycosylation profile of mature, or mature and activated, LCs:

In the first, the mouse skin was cut into approximately 1 cm$^2$ by 1 cm$^2$ pieces and incubated for 2 hours at 37° C. with dispase II to separate the dermis from the epidermis. The epidermis was subsequently disaggregated with trypsin to purify the LCs.

The second strategy consisted in differentiating the LCs from bone marrow as described by Ilarregui et al., 2009, supplemented by a culture medium with TNF-α (10 ng/ml) y TGF-β1 (20 ng/ml) for 7 days.

The LCs thus obtained by these two strategies were then either incubated for 24 hours with poly(I:C) (10 μg/ml) or not. A glycosylation pattern was determined by flow cytometry using biotinylated lectins: byotinylated SNA (20 μg/ml; E-YLabs), byotinylated PHA (10 μg/ml; Vector), byotinylated LEL (10 μg/ml; Vector), as described above (Toscano et al., 2007). In turn, the LCs were identified by antibody markers: 0.25 μg/tube of anti-CD207-FITC (clone RMUL.2; eBioscience) and 0.125 μg/tube of anti-CD11b-APC (clone M1/70; eBioscience). Finally, the cells were washed, resuspended and fixated in 200 μl of paraformaldehyde at 1% v/v until their analysis by flow cytometry in a BD FACSCanto flow cytometer.

In Vivo Epithelial Inflammation Models

Psoriasis:

The dorsal regions of 8- to 12-week-old mice were shaved prior to treatment (day 0 of the schedule described further below). A model of murine psoriasis was used, as described by Van Bell et al., (2011) induced by topical application of 0.25 g of Imiquimore-Imiquimod (PANALAB laboratories) on the backs of WT, Lgals7$^{-/-}$, and transgenic mice for Gal-7.

(Week 1) The first stage consisted in a disease induction period by daily applications of 0.25 g of Imiquimod (an agonist of the Toll-like receptor 7 (TLR7)) for 5 running days in WT, Lgals7–/–, and transgenic mice for Gal-7.

For each assay, 9 mice from each of the three genotypes were used. At the end of week 1 of treatment, 3 mice from each group were sacrificed to obtain samples of skin and of draining inguinal lymph nodes.

Figure 9:
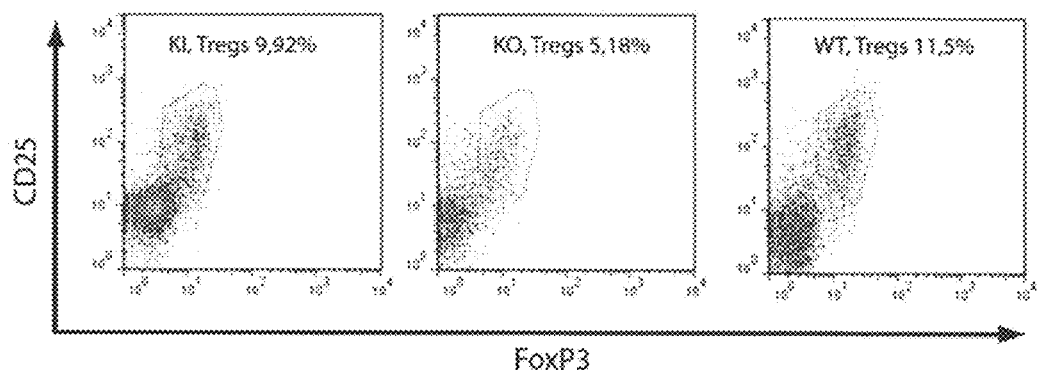
FIG. 9 Cytometry of Draining Lymph Nodes Cells after Irritant Dermatitis: Diagrams of cell populations analyzed by flow cytometry, where Treg lymphocytes (Foxp3+) are observed in the draining lymph nodes of the neck. After 3 days of treatment, KO mice exhibited a lower percentage of Treg lymphocytes in these ganglia.

(Week 2) On day 7, the second treatment period began only with WT and Lgals7–/– mice. The remaining 6 mice from both genotypes were divided into two groups: one group treated every day with 100 μg of recombinant Gal-7 (rGal7) in 0.1 g of neutral ointment applied to the affected area, with an application of 0.25 g of Imiquimod to sustain the inflammatory stimulus. The rGal-7 and Imiquimod application protocol schedule is described in detail in FIG. 9.

On the other hand, the control group mice of both genotypes were subjected to the same treatment described above in FIG. 9; only that 0.1 g of the neutral ointment without rGal-7 was applied on days 7, 9, and 11. At the end of week 2, the same procedures were performed on samples of skin and draining lymph nodes to evaluate the evolution of the disease.

Contact Irritation:

8 to 12-week-old mice were subjected to a skin inflammation treatment, which consisted in the application of 20 μl of PMA (Phorbol 12-myristate 13-acetate; Sigma) 35 mM on the right ear of the animals for three running days. On the left ear, 20 μl of ethanol at 70% (vehicle) was applied.

At the end of the three-day treatment, the mice were sacrificed and samples from the ears were obtained to analyze the leukocyte infiltrate by flow cytometry and confocal microscopy. In addition, the draining lymph nodes located close to the salivary ganglion region were processed for staining by flow cytometry.

Cell Culture of Draining Lymphatic Nodes

Draining lymph nodes cells were cultured for 3 days in a U-bottom, 96-well plate in RPMI+10% v/v FBS. Half the wells were re-stimulated with 400 UI/ml of rIL-2 and 10 ng/ml of rIL-23 (R&D), leaving the other half unstimulated as control. At the end of day 3, the conditioned media were collected for cytokines analysis and the cells were processed to analyze the percentage of Treg lymphocytes by flow cytometry and cellular proliferation by the addition of [$^3$H]-thymidine.

Immunofluorescence

Skin segments (from the ears and backs of mice) were embedded in Cryoplast to cut into 30 μm serialized sections with cryostat. These sections were used to evaluate the leukocyte infiltrate. In short, each slide was fixed for 15 min with paraformaldehyde at 4%, washed with PBS 1× (137 mM of NaCl; 2.7 mM of KCl; 8.1 mM of Na2HPO4; 1.5 mM of KH2PO4; pH at 7.2 to 7.4). The tissues were blocked with PBS 10% FBS (fetal calf serum) in a humid chamber for at least 40 minutes and subsequently incubated with specific antibodies for 24 hours at 4° C. in the dark. Sections were then washed and incubated with the secondary antibody conjugated to fluorochrome (FITC). The following antibodies were used as markers:

- 5 μg/ml polyclonal rabbit anti-mouse Gal-7 (Abcam, ab10482)
- 5 μg/ml polyclonal goat anti-rabbit-FITC (BD 554020)
- 2.5 μg/ml Anti-F4/80-FITC (clone BM8; eBioscience
- 2.5 μg/ml Anti-NK1.1-FITC (clone NBP1-28105; Novus Biological)
- 2.5 μg/ml de Anti-CD4-FITC (clone RM4-5; eBioscience)
- 5 μg/ml Anti-CD-207-FITC (clone RMUL.2; eBioscience)

Finally, the nuclei were dyed with propidium iodide or Hoechst (antifade), mounted, and stored at −20° C. until analysis.

Statistics

Prism software was used (GraphPad) for statistical analysis. When the two groups were compared, the Student test was used for unmatched data. For multiple comparisons, One-Way ANOVA was used, followed by Dunnett's, Tukey, or Bonferroni tests, as appropriate. Nonparametric analyses were performed using the Kruskal-Wallis test. p values lower or equal to 0.05 were considered significant.

Regulation of Gal-7 Expression in Murine and Human Keratinocytes

Evaluating the expression of Gal-7 in different murine tissues, taking into account tissues where their expression had been described in the literature. Based on total protein extracts from various organs, Gal-7 is expressed preferentially in the skin (as described in literature), as well as in the intestinal epithelium and the spleen (FIG. 1A). In the skin, as observed in the cryostat sections, Gal-7 expression by keratinocytes (immunofluorescence) is not homogeneous. On the other hand, it was observed that there was a higher epithelial expression of Gal-7 in the regions adjacent to the hair follicles. This differential distribution of Gal-7 expression coincides with the distribution of the precursor cells of Langerhans cells (LCs) in the epidermis.

Evaluation of whether the keratinocyte expression of Gal-7 can be regulated by particular stimulus. In this sense, primary cultures of murine keratinocytes and a cell line of immortal human keratinocytes (HaCaT) were incubated with different cytokines or Pathogen-Associated Molecular Patterns (PAMPs). In particular, FIGS. 1B-1F that IL-10, IL-12, TGF-β1, and TNF-α show the cytokines that determined a greater increase in the expression of Gal-7 in cell cultures as revealed in WB assays.

As observed in FIG. 1, Gal-1 expression in both cultures (human or murine keratinocytes) is not modulated by the different cytokines assayed (FIGS. 1C and 1D). This result shows that there is a differential regulation of the expression of Gal-7, but not of Gal-1, in these cell types (FIGS. 1E and 1F).

Figures 2A, 2B:
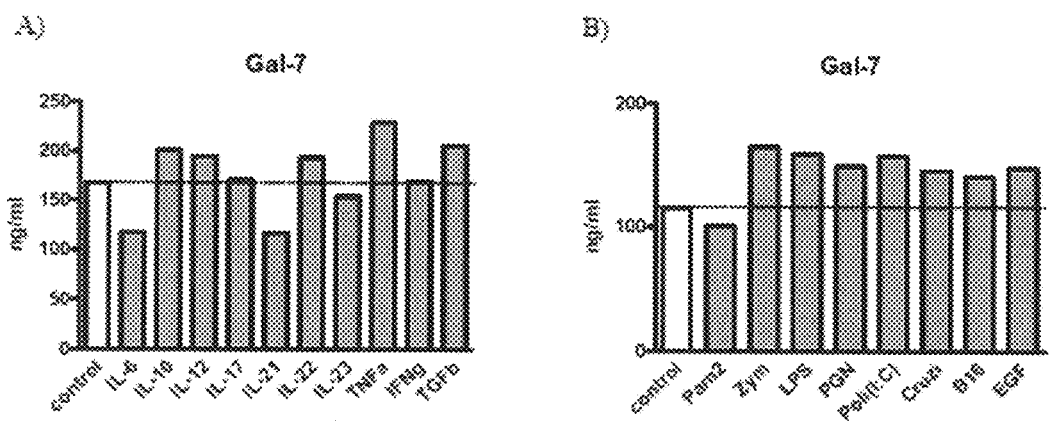
FIGS. 2A-2B Differential secretion of Gal-7: Quantification of Gal-7 secretion by primary keratinocyte murine cultures stimulated with: 2A) pro- and anti-inflammatory cytokines; 2B) pathogen-associated molecular patterns. A representative experiment is shown from a total of 3 with similar results.

Later, the levels of Gal-7 secreted by the keratinocytes to the extracellular environment upon stimulation as indicated above were evaluated. Variations in the levels of Gal-7 in the conditioned media were observed in reply to the different cytokines used in the cultures, in particular, IL-10, IL-12, TGF-β1, and TNF-α increased Gal-7 secretion, as revealed in the ELISA assays (p<0.05). (FIG. 2).

Subsequently, immunofluorescence assays were carried out using anti-Langerin-FITC and anti-Gal-7-Texas Red to stain the normal epidermis of C57CL/6J WT mice. An important distribution of Langerin was observed forming a sort of "immunological surveillance" that colocalizes with Gal-7. Nevertheless, this colocalization of Gal-7 and Langerin does not necessarily imply that the LCs express lectin (as shown in the WB figure); on the contrary, it might indicate a possible interaction between lectin and the glycan decorating the LC membrane proteins (FIGS. 3A and 3B).

Differential Glycosylation in Murine LCs

Figure 4B:
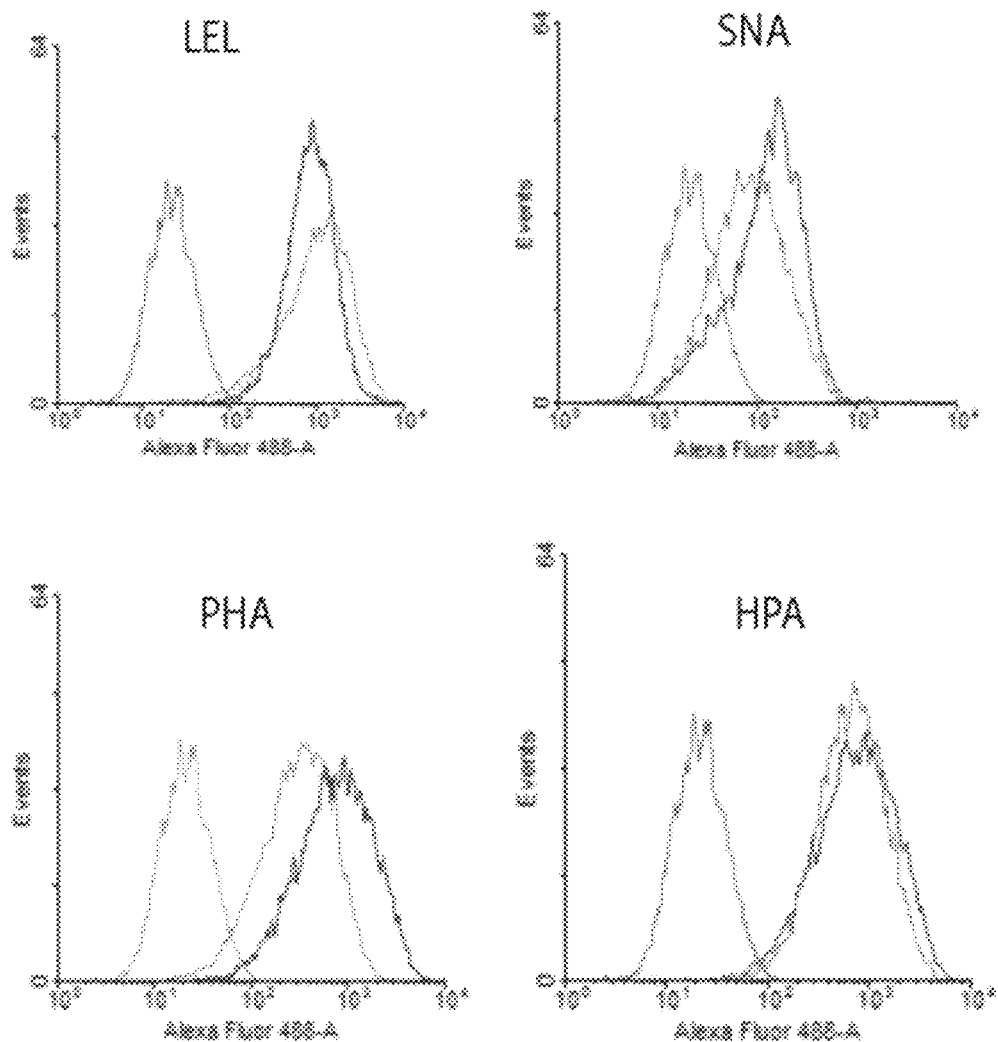
Figure 4C:
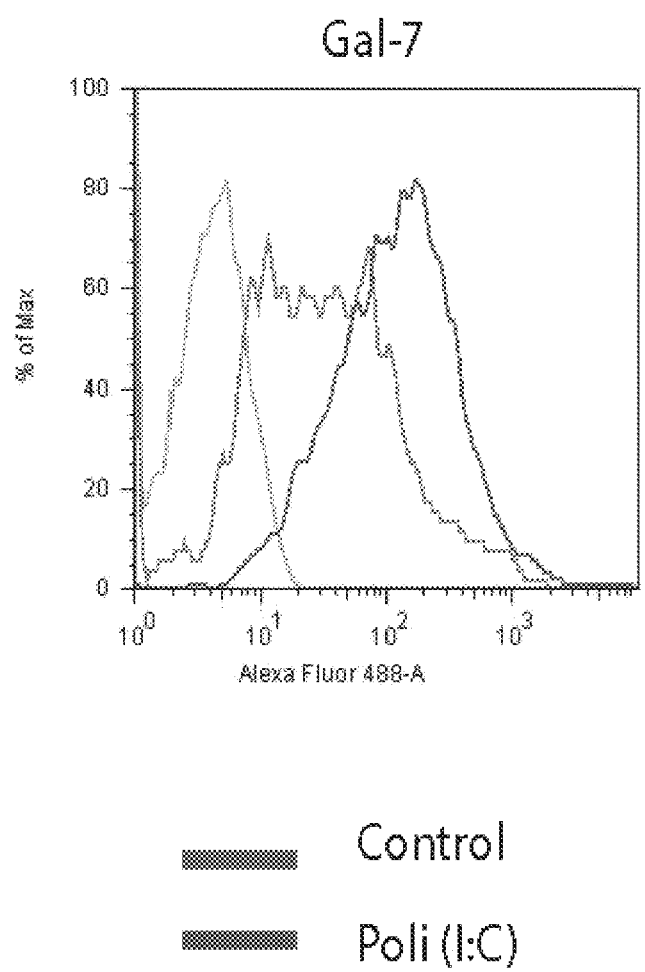

Based on the observation of a possible interaction between LCs and Gal-7, the working premise was whether this bond could be modulated by the physiology of LCs upon activation. Hence, the surface glycans of LCs was analyzed, whether activated with poly(I:C) (captured by TLR3 receptors) or not (control). These studies indicated that the LCs activated with the TLR agonist for 24 hours showed an increase in sialylation of the membrane glycans in the α2,6 position (an effect observed by means of the lectin marker (SNA), and it also reveals the presence of complex N-glycans (an increase in binding of the PHA lectin) and of poly-N-acetyllactosamine repeats (increase in binding of the LEL lectin) (FIG. 4).

The result shows that when the LCs are activated they switch their glycophenotype, increasing the binding of Gal-7. On the other hand, binding of Gal-1 to LacNac repeat units is sterically hindered because of higher sialylation in the α-2,6 position of the membrane glycoproteins.

Impact of Gal-7-Activated LCs in Proliferation and Differentiation Assays with Naïve T Lymphocytes Based on these findings, where activated LCs modified their glycophenotype, promoting higher binding of Gal-7, the example evaluated the physiological effect of this interaction by analyzing LCs exposed to the action of Gal-7 and its impact on the associated T response. In this sense, LCs from bone marrow precursors were differentiated. Once the LCs are differentiated, they were activated with poly(I:C) either in the presence of growing concentrations of rGal-7 or not. Twenty-four hours later, the conditioned media from activated LCs were collected and then the secretion of TGF-β1, IL-10, and IL-27 (tolerogenic cytokines) was assayed by ELISA. There was higher secretion of these cytokines by activated LCs dependent on concentrations of rGal7 (FIGS. 5B-5D).

Figures 5A, 5B, 5C, 5D:
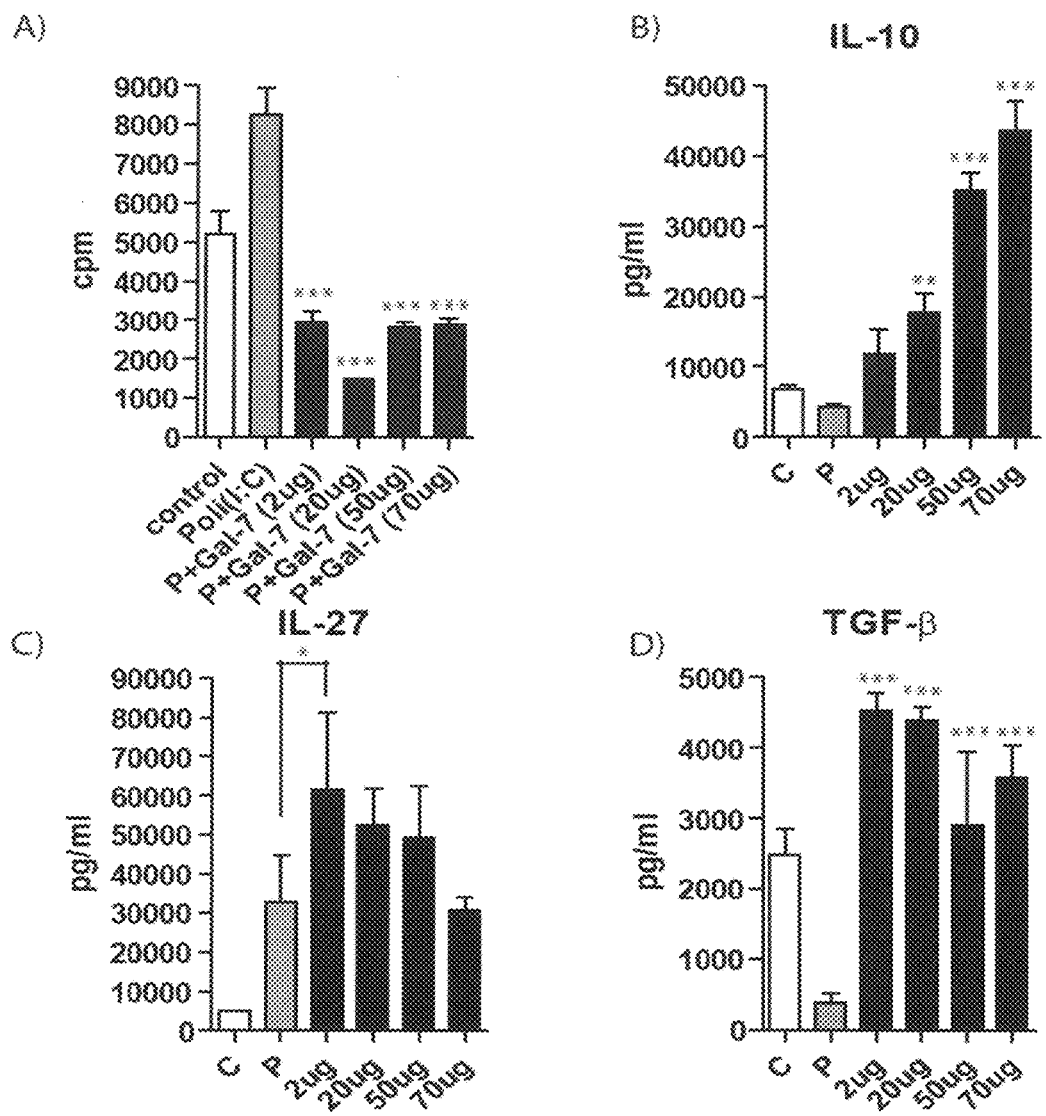
FIGS. 5A-5D Gal-7 Promotes a Tolerogenic Phenotype to LCs: 5A) Proliferation suppression assay on spleen cells, where LCs pre-incubated with rGal-7 inhibits cell proliferation; 5B-D) Quantification of cytokine secretion during LC activation, pre-incubated with different concentrations of rGal-7. (*$p<0.05$; $p<0.01$; *$p<0.001$ as opposed to treatment with only poly(I:C), "P").

Subsequently, the capacity of these LCs to stimulate or suppress the proliferation of spleen cells in a mixed lymphocyte culture was analyzed (FIG. 5A). LCs activated in the absence of rGal-7 were observed to be capable of stimulating the proliferation of splenocytes, whereas LCs activated and pre-incubated with different concentrations of rGal-7 were found to promote a tolerogenic phenotype capable of suppressing the proliferation response of splenocytes, dependent on the dosage (FIG. 5).

Subsequently, naïve T lymphocyte purified by cytometry using CD4 and CD62L markers from spleen cells, were co-cultured with: 1) LCs pre-incubated with rGal-7 and activated; or 2) LC conditioned media (FIG. 6). After three days, co-culture conditioned media were analyzed by ELISA (IFN-γ, IL-17, and IL-22) (FIG. 7), and the percentage of CD4+CD25+FoxP3+ Treg cells was evaluated by flow cytometry assays (FIG. 6). LCs activated in the presence of rGal-7 were observed to induce cell differentiation of naïve T cells to a regulatory profile (Treg) dependent on the concentration of this lectin. This same effect was observed when naïve T lymphocytes were incubated with conditioned media from LC activation described above (FIG. 6).

Figures 7A, 7B, 7C, 7D:
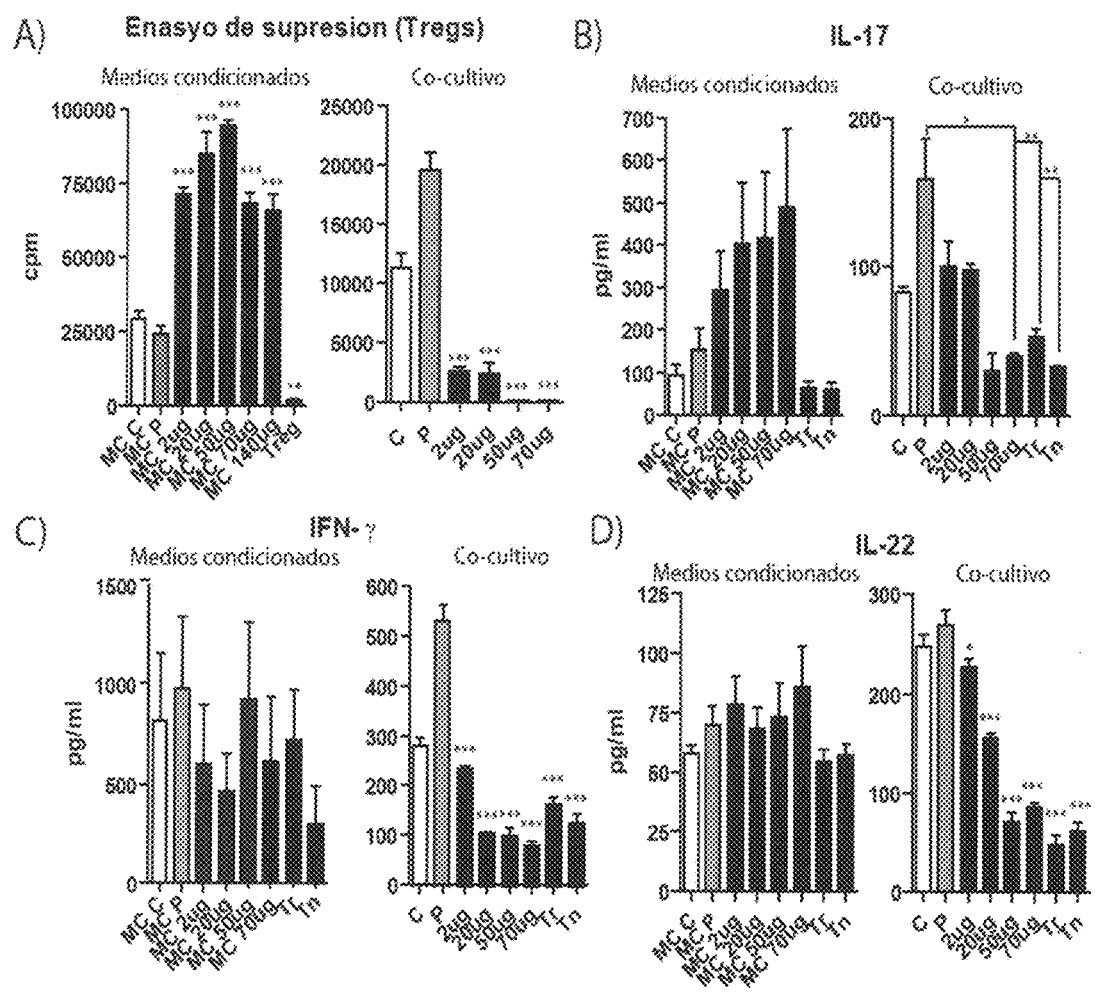
FIGS. 7A-7D Suppressor capacity of Tregs induced by LCs activated in presence of Gal-7: 7A) Proliferation suppression assay by Tregs differentiated from naïve T cells incubated with conditioned media of activated LCs (CM) (left) or from co-cultures with LCs (right); 7B-D) T-cell differentiation profiles according to the cytokine secretion pattern during differentiation of naïve T cells with conditioned media from control LCs (C), activated LCs (P), or activated and pre-incubated with different concentrations of rGal-7 (X µg of rGal-7) (left), or in co-culture with LCs under the same conditions described before (right). (*$p<0.05$; $p<0.01$; *$p<0.001$ in relation to "CM P" in the corresponding histograms of conditioned media assays, or in relation to "P" in the corresponding histograms of co-cultures with LCs assays).

However, Treg cells differentiated by the conditioned media of the LCs in the presence of Gal-7 were unable to suppress lymphocyte proliferation in MLR assays. By contrast, Tregs from the co-culture of naïve T lymphocyte and LCs effectively have suppressor capacity (FIG. 7A). Moreover, opposite results were observed in relation to secretion in inflammatory cytokines, i.e., a decrease in secretion of IL-22, IL-17, and IFN-γ (dependent on the concentration of Gal-7) in co-cultures with LCs compared with conditioned media (FIGS. 7B-7D), pointing to the importance of cell-to-cell contact between LCs and T lymphocytes for promoting a Gal-7-induced suppressor phenotype.

The results show that Gal-7 is involved in regulating of the epithelial immune system. This effect would translate into maturation of LCs to an immuno-regulator profile (or tolerogenic), characterized by high secretion of IL-10, IL-27, and TGF-β1. These tolerogenic LCs, when migrating to draining lymph nodes may induce differentiation of naïve T lymphocytes to iTreg profile, and not to pro-inflammatory Th1, Th17, and Th22 profiles (FIGS. 6 and 7).

Cutaneous Inflammation in WT, Gal-7-Deficient, and Transgenic for Gal-7 Mice

In the context of in vitro assays, this example analyzes each of the components involved in the immunological circuit of the skin, from keratinocytes and LCs in the epidermis to T lymphocytes in the draining lymph nodes. The data established that the presence of Gal-7 in the culture medium during LC activation is translated into differential maturation, where these LCs, through cell-to-cell contact, induce higher differentiation of naïve T cells to a regulatory profile with increased suppressor capacity.

The next objective of this work was to confirm this circuit proven in vitro by studying in vivo inflammatory models. The study proceeded to use two cutaneous inflammation models (psoriasis and irritant dermatitis) in three murine strains: C57BL/6J wild type (WT), transgenic for Gal-7 (Tg), and Gal-7-deficient (Lgals7$^{-/-}$ or KO).

Inflammatory Dermatitis

Figure 8A:
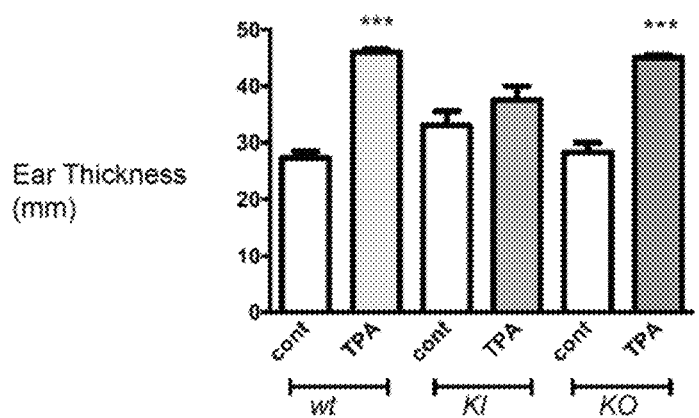
FIGS. 8A-8E Irritant Dermatitis: 8A) Quantification of ear thickness after 3 days of irritation. KO mice exhibited greater inflammation in the ears compared with WT and Tg mice (***$p<0.001$ compared with the control ear thickness for each genotype); 8B) and 8C) Percentage of LCs in murine ears after three days of inflammation. KO mice exhibited a higher percentage of LCs in the epidermis; 8D) Quantification of epidermal thickness; 8E) Immunofluorescence for cell infiltrate in the ears. (*$p<0.05$; $p<0.01$; *$p<0.001$)

As a first assay on cutaneous inflammation, inflammatory dermatitis was induced in the ears of C57BL/6J WT, Tg, and KO mice by topical application of TPA for 3 running days. Throughout this inflammatory process, thickness of the treated ears was measured every day and compared with baseline and contralateral ear thicknesses, where 70% ethanol (vehicle) was applied. It was found that the ear treated with the irritant increased its thickness day by day, as an indicator of inflammation. Based on the hypothesis, the inflammation was greater in Lgals7$^{-/-}$, and WT mice compared with Tg animals that overexpressed the lectin (FIG. 8A).

These results show that Gal-7 is involved in regulating of the epithelial immune system. This effect would translate into maturation of LCs to an immuno-regulator profile (or tolerogenic), characterized by high secretion of IL-10, IL-27, and TGF-β1. These tolerogenic LCs, when migrating to draining lymph nodes may induce differentiation of naïve T lymphocytes to iTreg profile, and not to pro-inflammatory Th1, Th17, and Th22 profiles (FIGS. 6 and 7).

Figures 8B, 8C:
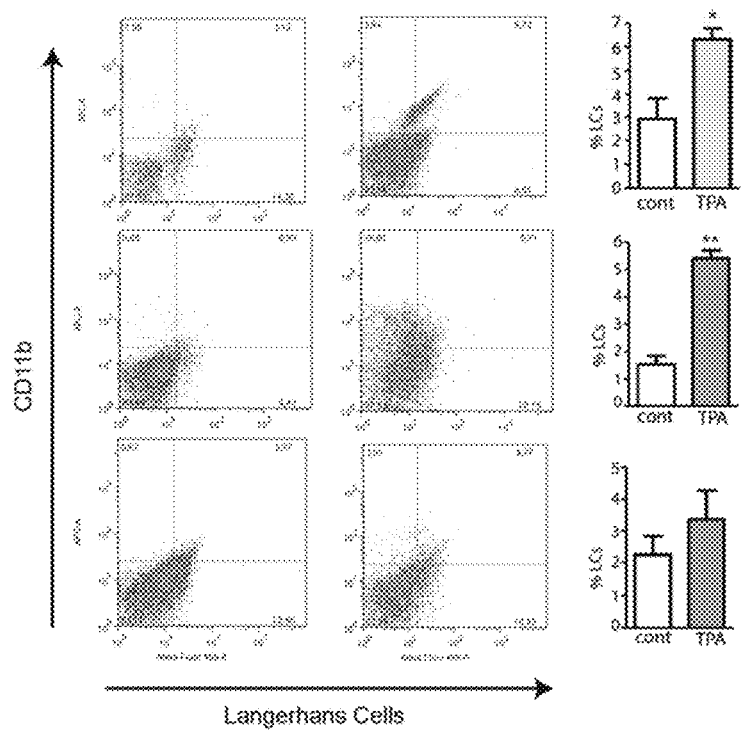
Figure 8D:
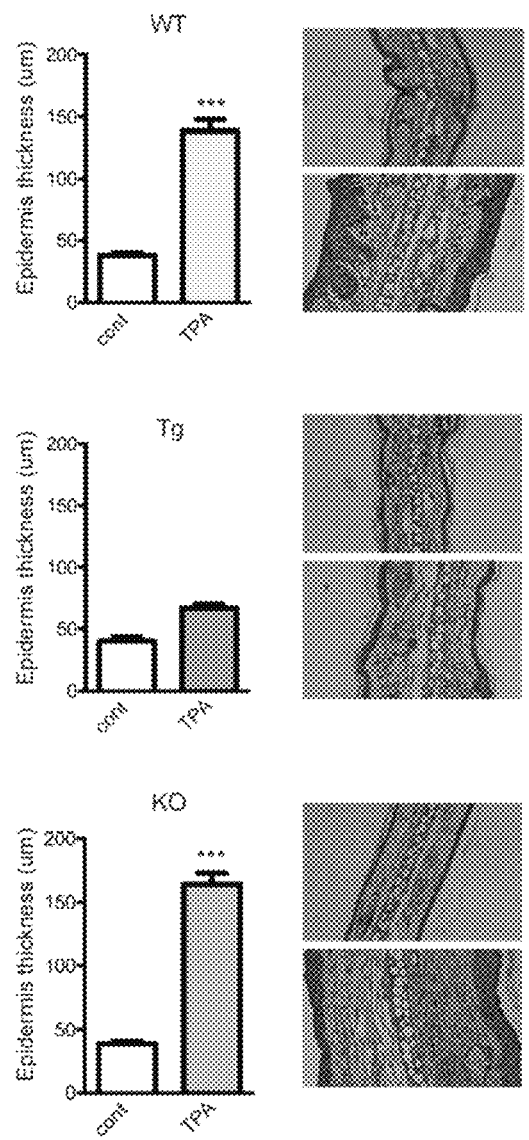

Based on the results of flow cytometry assays on epidermal cell suspensions, a greater frequency of LCs in Gal-7-deficient murine ears was observed after three days of treatment (FIGS. 8B and 8C). Likewise, greater thickness in the epidermis of the ears treated with TPA was observed in the histological sections of the irritated area when compared with the controls in WT and KO animals (FIG. 8D).

Figure 8E:
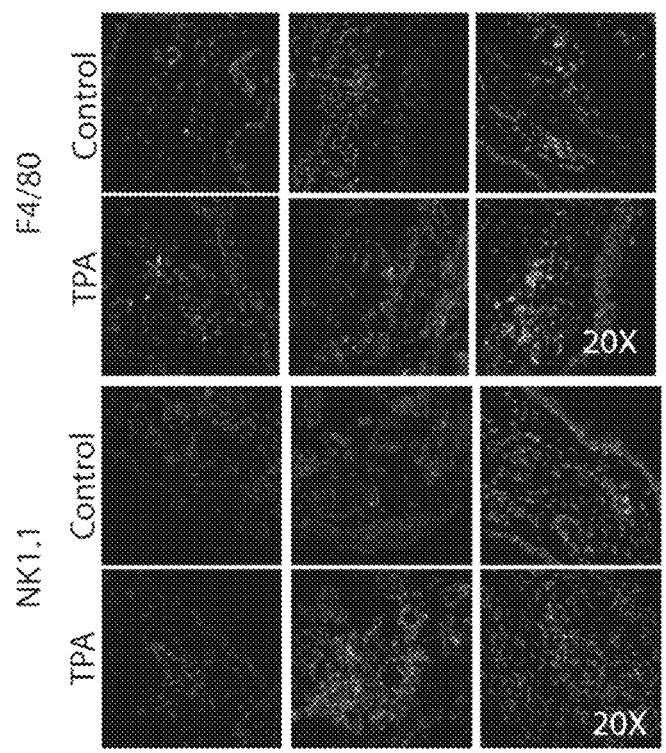

This effect is accompanied with a higher infiltration of macrophages and NK cells in the skin of these ears (FIG. 8E). Furthermore, less frequency of Treg lymphocytes was observed through flow cytometry (FIG. 9) in the draining neck lymph nodes of KO mice compared with mice from the other two genotypes.

This effect is accompanied with a higher infiltration of macrophages and NK cells in the skin of these ears (FIG. 8E). Furthermore, less frequency of Treg lymphocytes was observed through flow cytometry (FIG. 9) in the draining neck lymph nodes of KO mice compared with mice from the other two genotypes.

Psoriasis

Figures 10A, 10B, 10C, 10D:
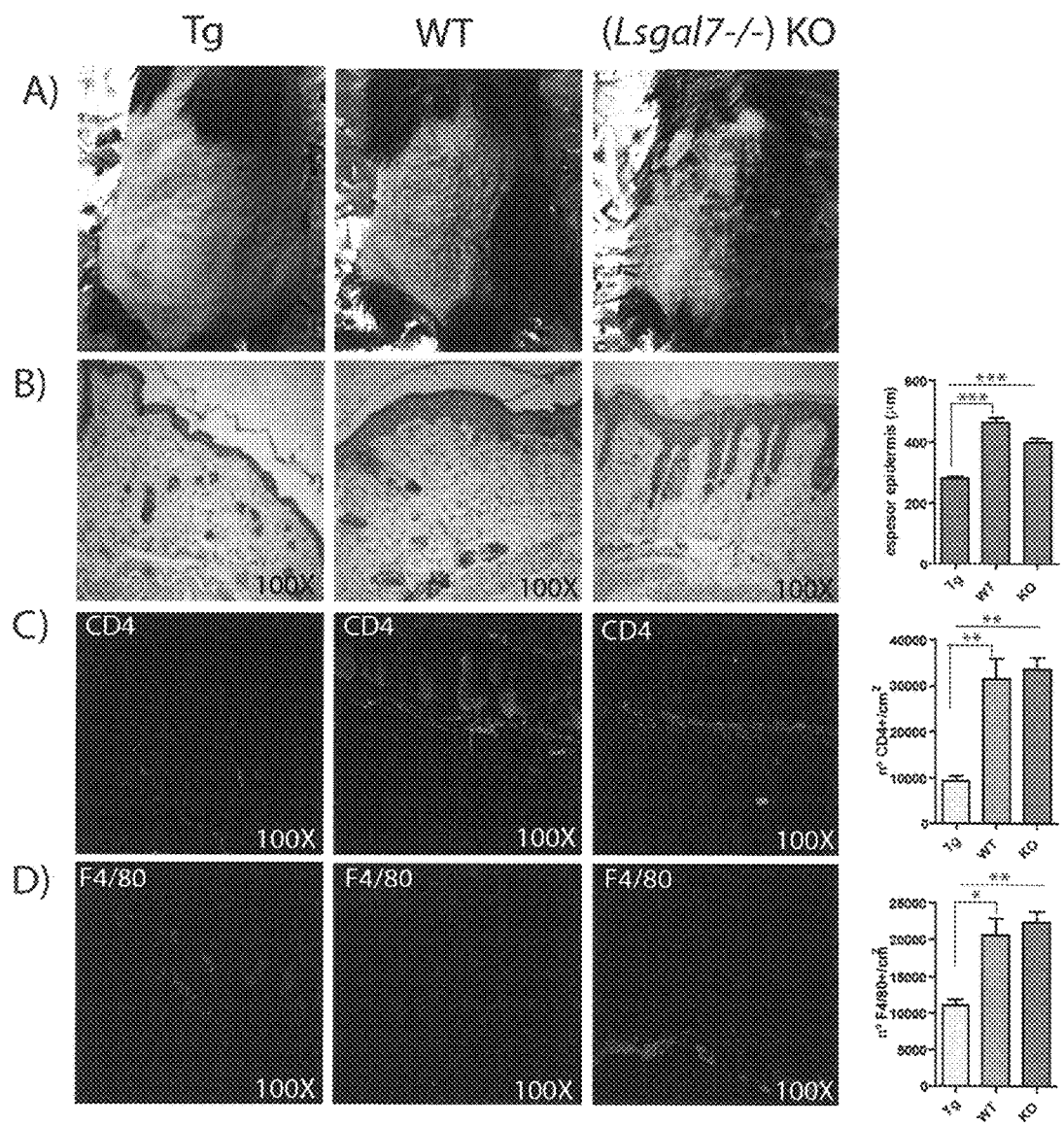
FIGS. 10A-10D Histopathological Manifestations of Psoriasis in Week One: 10A) Images of the backs of WT, KO, and Tg mice treated with Imiquimod for 5 running days. 10B) Images of histological sections dyed with hematoxylin and eosin. The histograms illustrate murine epidermal thickness. 10C and 10D) Images of immunofluorescence with 10C) anti-CD4 and 10D) anti-F4/80 antibodies conjugated to fluorochromes. The histograms show leukocyte density in the infiltrate of the treated mice. (*$p<0.05$; $p<0.01$; *$p<0.001$)

Following the model described by Van Bell et al., 2011, the mice were treated for 5 running days with a topical application of Imiquimod (TLR 7 agonist). At the end of the treatment, mice from the three genotypes mentioned above exhibited different clinical symptomatology and histopathological manifestations. In particular, WT and KO mice exhibited large erythematous plaques and, through histological sections, a notable increase in the thickness of the epidermis was observed (acanthosis). After a thorough analysis, we inferred that the transgenic mice exhibited a lower increase in epidermal thickness compared with WT mice and, in turn, WT mice showed less pathology when compared with Gal-7-deficient mice (FIG. 10A). Using specific antibodies on cryostat skin sections, we have observed the presence of CD4+ T lymphocytes and macrophages in treated animals by immunofluorescence (FIG. 10B). In this sense, Gal-7-deficient mice have a higher cell infiltrate compared with transgenic and WT mice. In addition, a lower percentage of Treg lymphocytes was observed in draining inguinal lymph nodes in Gal-7-deficient mice compared with the other two genotypes (results not shown).

In addition, the study proceeded to perform ex vivo assays. In this sense, cells from draining inguinal lymph nodes were cultured for 3 days, either with or without stimulation of rIL-2 and rIL-23.

According to the literature on the etiology of psoriasis, Th1 lymphocytes may be responsible for inducing initial skin irritation. On the other hand, once the inflammatory foci are established, it can be inferred that Th17 and Th22 lymphocytes may be the ones that perpetuate chronic skin inflammation. This is why the presence of these lymphocyte profiles was studied by analyzing the cytokine secretions characteristic of each one of them in the culture media of draining lymph nodes cells.

Figure 11A:
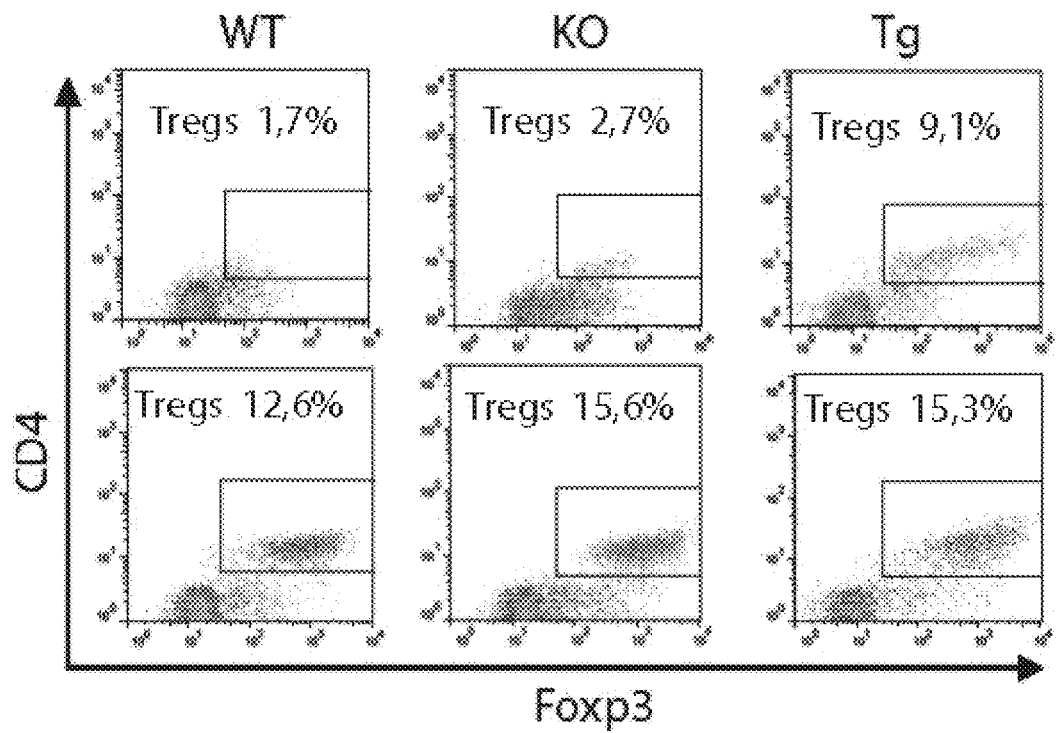
FIGS. 11A-11B Ex vivo re-stimulation of draining lymphatic node cells with rIL-2 and rIL-23: 11A) Flow cytometry where Foxp3+ Treg lymphocytes are observed in draining lymphatic node cell cultures. 11B) T cell differentiation profiles according to the cytokine secretion pattern during the ex vivo re-stimulation assay of draining lymphatic node cells. ($p<0.01$; *$p<0.001$)
Figure 11B:
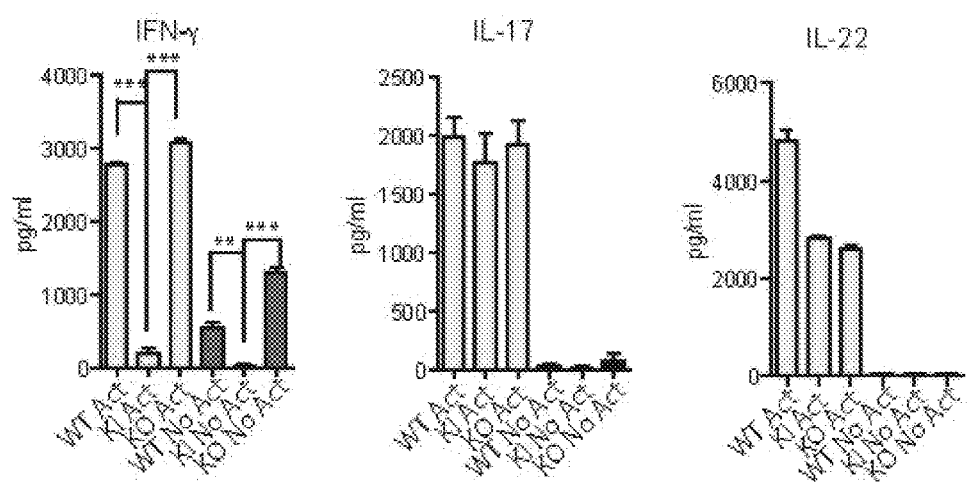

It was observed a significant decrease of IFN-γ secretion on the part of draining lymph nodes cells from transgenic mice (Tg) (FIG. 11C) Likewise, a higher frequency of Treg lymphocytes in the lymph nodes of Tg mice was observed in cultures without re-stimulation, compared with lymph nodes from mice of the other two genotypes (FIGS. 11A and 11B).

According to these results, it was have hypothesized that Treg cells inducing in draining lymph nodes of Tg mice may significantly modulate the inflammatory skin process, decreasing the frequency and the activity of Th1 lymphocytes and, therefore, diminishing the pathogenesis of psoriasis in mice with this genotype.

The therapeutic effect of Gal-7 in psoriatic WT and Gal-7-deficient mice at the end of one week of treatment with Imiquimod was studied. In this context, a topical treatment with recombinant Gal-7 (rGal7) was used on WT and KO mice (FIG. 12). As mentioned above, epidermal irritation increases permeability and, therefore, small molecules such as rGal-7 are able to penetrate the epidermis.

Figures 12A, 12B, 12C, 12D:
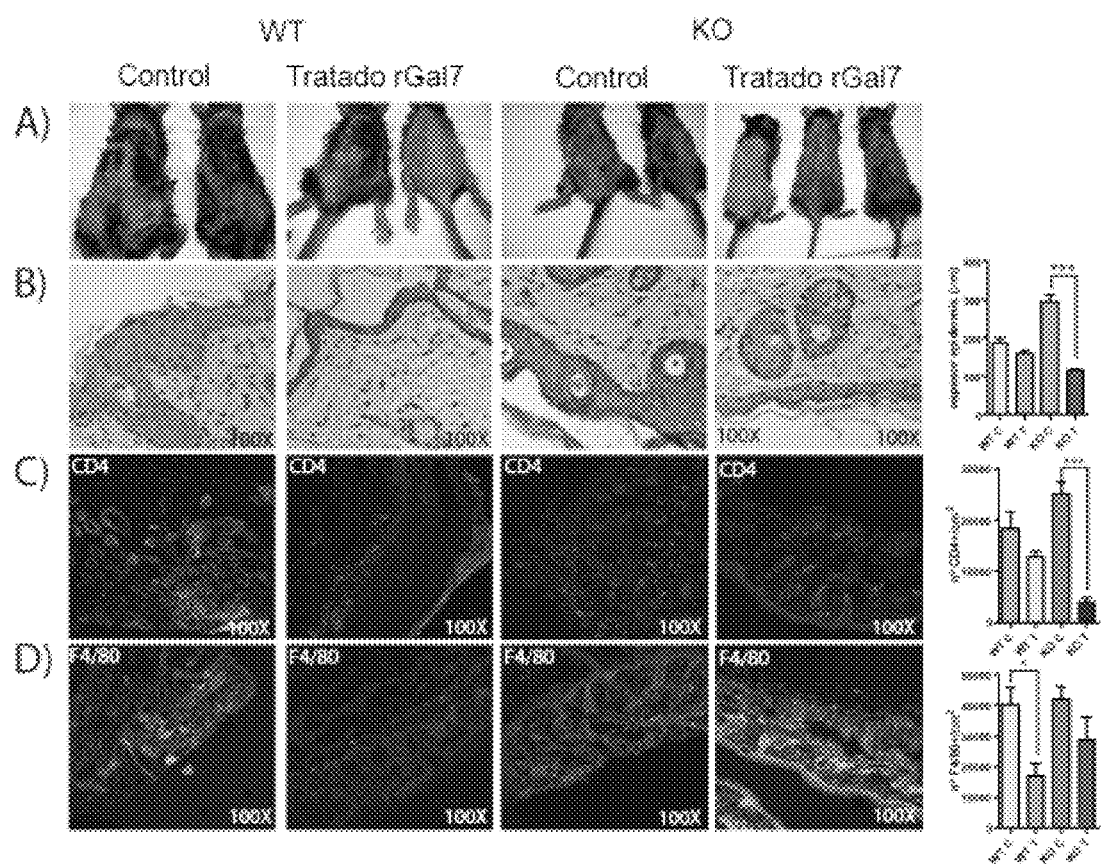
FIGS. 12A-12D Histopathological manifestations after treatment of psoriasis with rGal-7: 12A) Images of the backs of WT mice and KO mice treated with neutral ointment (control) or with neutral ointment and rGal-7 during week two of treatment. 12B) Images of histological sections dyed with hematoxylin and eosin. Histograms illustrate murine epidermal thickness. 12C and 12D) Images of immunofluorescence with 12C) anti-CD4 and 12D) anti-F4/80 antibodies conjugated with fluorochromes. Histograms show the differential leukocyte density in the infiltrate of the treated mice. (*$p<0.05$; ***$p<0.001$).

At the end of week two of treatment, topical application of rGal-7, alternating with the application of Imiquimod (used to maintain the inflammatory stimulus), exhibited a decrease in epidermal thickness. This decrease was even more evident in KO mice, compared with WT animals. This effect is partly due to the fact that epidermal thickness of WT mice reduced its size as a result of not receiving daily treatment with Imiquimod, as was the case in week one (FIGS. 12A and 12B). On the other hand, treatment with rGal-7 evidenced a reduction in the cell infiltrate (CD4+ and F4/80+) both in KO as well as WT mice (FIGS. 12C and 12D).

Therefore, using these two experimental cutaneous inflammation models, the results obtained in the in vitro assays was corroborated. Higher levels of Gal-7 in the skin (Tg mice or mice treated with rGal-7) contributed to the resolution of the inflammation, by inducing the LCs, which upon activation, acquired a regulatory profile. These LCs stimulate the differentiation of naïve T lymphocytes to regulatory T profile, and these cells are ultimately in charge of limiting cutaneous inflammation.

The detailed example set forth above is provided to aid those skilled in the art in practicing the invention. However, the invention described and claimed herein is to be limited in scope by the specific embodiments described above, as these embodiments are presented as mere illustrations of several aspects of the invention. Any combinations and modifications of the described methods and components, and compositions used in the practice of the methods, in addition to those not specifically described, will become apparent to those skilled in the art based on the present disclosure and do not depart from the spirit or scope of the present invention. Such variations, modifications, and combinations are also encompassed by the present disclosure and fall within the scope of the appended claims.

REFERENCES

1. Abrams J R, Kelley S L, Hayes E, Kikuchi T, Brown M J, Kang S et al. Blockade of T lymphocyte costimulation with cytotoxic T lymphocyte associated antigen 4-immunoglobulin (CTLA4Ig) reverses the cellular pathology of psoriatic plaques, including the activation of keratinocytes, dendritic cells, and endothelial cells. J Exp Med. 2000; 192:681-94
2. Allan S E, Song-Zhao G X, Abraham T, McMurchy A N, Levings M K. Inducible reprogramming of human T cells into Treg cells by a conditionally active form of FOXP3. Eur J immunol. 2008; 38(12):3282-9.
3. Awasthi A, Riol-Blanco L, Jager A, Korn T, Pot C, Galileos G, et al. Cutting edge: IL-23 receptor gfp reporter mice reveal distinct populations of IL-17-producing cells. J immunol. 2009; 182(10):5904-8.
4. Baadsgaard O, Fisher G, Voorhees J J, Cooper K D. The role of the immune system in the pathogenesis of psoriasis. J Invest Dermatol. 1990; 95(5):325-45.
5. Baran W, Szepietowski J C, Szybejko-Machaj G. Expression of p53 protein in psoriasis. Acta dermatovenerologica Alpina, Panonica, et Adriatica. 2005; 14(3):79-83.
6. Bernerd F, Sarasin A, Magnaldo T. Galectin-7 overexpression is associated with the apoptotic process in UVB-induced sunburn keratinocytes. Proc Natl Acad Sci USA. 1999; 96(20):11329-34.
7. Biron-Pain K, Grosset A A, Poirier F, Gaboury L, St-Pierre Y. Expression and functions of galectin-7 in human and murine melanomas. PloS ONE. 2013; 8(5):e63307.
8. Bursch L S, Wang L, Igyarto B, Kissenpfennig A, Malissen B, Kaplan D H, et al. Identification of a novel population of Langerin+ dendritic cells. J Exp Med. 2007; 204(13):3147-56.
9. Cao, Z., Said, N., Amin, S., Wu, H. K., Bruce, A., Garate, M., Hsu, D. K., Kuwabara, I., Liu, F. T., and Panjwani, N. Galectins-3 and -7, but not galectin-1, play a role in re-epithelialization of wounds. J. Biol. Chem. 2002; 277, 42299-42305.
10. Cao, Z., Said, N., Wu, H. K., Kuwabara, I., Liu, F. T., and Panjwani, N. Galectin-7 as a potential mediator of corneal epithelial cell migration. Arch. Ophthalmol. 2003; 121, 82-86.
11. Delgado V M, Nugnes L G, Colombo L L, Troncoso M F, Fernandez M M, Malchiodi E L, et al. Modulation of endothelial cell migration and angiogenesis: a novel function for the "tandem-repeat" lectin galectin-8. FASEB J 2011; 25(1):242-54.
12. Caruso R, Botti E, Sarra M, Esposito M, Stolfi C, Diluvio L, et al. Involvement of interleukin-21 in the epidermal hyperplasia of psoriasis. Nat Med 2009; 15(9):1013-5.
13. Ciric B, El-behi M, Cabrera R, Zhang G X, Rostami A. IL-23 drives pathogenic IL-17-producing CD8+ T cells. J Immunol. 2009; 182(9):5296-305.
14. Cooper D N. Galectinomics: finding themes in complexity. Biochim Biophys Acta. 2002; 1572(2-3):209-31
15. Croci D O, Cerliani J P, Dalotto-Moreno T, Mendez-Huergo S P, Mascanfroni I D, Dergan-Dylon S, et al. Glycosylation-Dependent Lectin-Receptor Interactions Preserve Angiogenesis in Anti-VEGF Refractory Tumors. Cell 2014; 156(4):744-58.
16. Curotto de Lafaille M A, Lafaille J J. Natural and adaptive foxp3+ regulatory T cells: more of the same or a division of labor? Immunity. 2009; 30(5):626-35.
17. Demetriou M, Granovsky M, Quaggin S, Dennis J W. Negative regulation of T-cell activation and autoimmunity by Mgat5 N-glycosylation. Nature. 2001; 409(6821):733-9.
18. Edelson B T, Kc W, Juang R, Kohyama M, Benoit L A, Klekotka P A, et al. Peripheral C D103+ dendritic cells form a unified subset developmentally related to CD8alpha+ conventional dendritic cells. J Exp Med 2010; 207(4):823-36.
19. Gagliani N, Magnani C F, Huber S, Gianolini M E, Pala M, Licona-Limon P, et al. Coexpression of CD49b and LAG-3 identifies human and mouse T regulatory type 1 cells. Nat Med. 2013 19(6):739-46.
20. Gendronneau G, Sidhu S S, Delacour D, Dang T, Calonne C, Houzelstein D, et al. Galectin-7 in the control of epidermal homeostasis after injury. Mol Biol Cell. 2008; 19(12):5541-9.
21. Goedkoop A Y, de Rie M A, Picavet D I, Kraan M C, Dinant H J, van Kuijk A W, et al. Alefacept therapy reduces the effector T-cell population in lesional psoriatic epidermis. Arch Dermatol Res 2004; 295(11):465-73.
22. Ghoreishi M, Bach P, Obst J, Komba M, Fleet J C, Dutz J P. Expansion of antigen-specific regulatory T cells with the topical vitamin d analog calcipotriol. J immunol. 2009; 182(10):6071-8.

23. Hemmi H, Yoshino M, Yamazaki H, Naito M, Iyoda T, Omatsu Y, et al. Skin antigens in the steady state are trafficked to regional lymph nodes by transforming growth factor-beta1-dependent cells. Int Immunol 2001; 13(5):695-704.
24. Honda T, Egawa G, Grabbe S, Kabashima K. Update of immune events in the murine contact hypersensitivity model: toward the understanding of allergic contact dermatitis. J Invest Dermatol. 2013; 133(2):303-15.
25. Igyarto B Z, Jenison M C, Dudda J C, Roers A, Muller W, Koni P A, et al. Langerhans cells suppress contact hypersensitivity responses via cognate CD4 interaction and langerhans cell-derived IL-10. J Immunol 2009; 183(8):5085-93.
26. Ilarregui J M, Croci D O, Bianco G A, Toscano M A, Salatino M, Vermeulen M E, et al. Tolerogenic signals delivered by dendritic cells to T cells through a galectin-1-driven immunoregulatory circuit involving interleukin 27 and interleukin 10. Nat Immunol 2009; 10(9):981-91.
27. Kaplan D H, Jenison M C, Saeland S, Shlomchik W D, Shlomchik M J. Epidermal langerhans cell-deficient mice develop enhanced contact hypersensitivity. Immunity. 2005; 23(6):611-20.
28. Kissenpfennig A, Henri S, Dubois B, Laplace-Builhe C, Perrin P, Romani N, et al. Dynamics and function of Langerhans cells in vivo: dermal dendritic cells colonize lymph node areas distinct from slower migrating Langerhans cells. Immunity. 2005; 22(5): 643-54.
29. Kopitz J, Andre S, von Reitzenstein C, Versluis K, Kaltner H, Pieters R J, et al. Homodimeric galectin-7 (p53-induced gene 1) is a negative growth regulator for human neuroblastoma cells. Oncogene. 2003; 22(40): 6277-88.
30. Leffler H, Carlsson S, Hedlund M, Qian Y, Poirier F. Introduction to galectins. Glycoconjugate J 2004; 19(7-9):433-40.
31. Lew W, Bowcock A M, Krueger J G. Psoriasis vulgaris: cutaneous lymphoid tissue supports T-cell activation and "Type 1" inflammatory gene expression. Trends Immunol 2004; 25(6):295-305.
32. Liu F T, Rabinovich G A. Galectins as modulators of tumour progression. Nat Rev Cancer. 2005; 5(1):29-41.
33. Madsen P, Rasmussen H H, Flint T, Gromov P, Kruse T A, Honore B, et al. Cloning, expression, and chromosome mapping of human galectin-7. J Biol Chem. 1995; 270 (11):5823-9.
34. Magnaldo, T., et al. (1995). "Galectin-7, a human 14-kDa S-lectin, specifically expressed in keratinocytes and sensitive to retinoic acid." Dev Biol 168(2): 259-271.
35. Magnaldo T, Fowlis D, Darmon M. Galectin-7, a marker of all types of stratified epithelia. Differentiation. 1998; 63(3):159-68.
36. Marble D J, Gordon K B, Nickoloff B J. Targeting TNFalpha rapidly reduces density of dendritic cells and macrophages in psoriatic plaques with restoration of epidermal keratinocyte differentiation. J Dermatoll Sci. 2007; 48(2):87-101.
37. Markowska A I, Liu F T, Panjwani N. Galectin-3 is an important mediator of VEGF- and bFGF-mediated angiogenic response. J Exp Med. 2010; 207(9):1981-93.
38. Marth J D, Grewal P K. Mammalian glycosylation in immunity. Nat Rev Immunol. 2008; 8(11):874-87.
39. Martin D A, Towne J E, Kricorian G, Klekotka P, Gudjonsson J E, Krueger J G, et al. The emerging role of IL-17 in the pathogenesis of psoriasis: preclinical and clinical findings. J Invest Dermatol. 2013; 133(1):17-26.
40. Noordegraaf M, Flacher V, Stoitzner P, Clausen B E. Functional redundancy of Langerhans cells and Langerin+ dermal dendritic cells in contact hypersensitivity. J Invest Dermatol 2010; 130(12):2752-9.
41. Rabinovich G A, Liu F T, Hirashima M, Anderson A. An emerging role for galectins in tuning the immune response: lessons from experimental models of inflammatory disease, autoimmunity and cancer. Scand J Immunol. 2007; 66(2-3):143-58.
42. Rabinovich G A, Toscano M A, Jackson S S, Vasta G R. Functions of cell surface galectin-glycoprotein lattices. Curr Opin Struct Biol 2007; 17(5):513-20.
43. Rabinovich G A, Toscano M A. Turning 'sweet' on immunity: galectin-glycan interactions in immune tolerance and inflammation. Nat Rev Immunol. 2009; 9(5): 338-52.
44. Roncarolo M G, Bacchetta R, Bordignon C, Narula S, Levings M K. Type 1 T regulatory cells. Immunol Rev 2001; 182:68-79.
45. Sakaguchi S. Naturally arising Foxp3-expressing CD25+CD4+ regulatory T cells in immunological tolerance to self and non-self. Nat Immunol. 2005; 6(4):345-52.
46. Salatino M, Croci D O, Bianco G A, Ilarregui J M, Toscano M A, Rabinovich G A. Galectin-1 as a potential therapeutic target in autoimmune disorders and cancer. Exp Opin Biol Ther 2008; 8(1):45-57.
47. Saussez S, Kiss R. Galectin-7. Cell Moll Life Sci. 2006; 63(6):686-97.
48. Sutton C E, Lalor S J, Sweeney C M, Brereton C F, Lavelle E C, Mills K H. Interleukin-1 and IL-23 induce innate IL-17 production from gammadelta T cells, amplifying Th17 responses and autoimmunity. Immunity. 2009; 31(2):331-41.
49. Tan C H, Rasool S, Johnston G A. Contact dermatitis: allergic and irritant. Clin Dermatol. 2014; 32(1):116-24.
50. Thijssen V L, Postel R, Brandwijk R J, Dings R P, Nesmelova I, Satijn S, et al. Galectin-1 is essential in tumor angiogenesis and is a target for antiangiogenesis therapy. Proc Natl Acad Sci USA 2006; 103(43):15975-80.
51. Timmons P M, Colnot C, Cail I, Poirier F, Magnaldo T. Expression of galectin-7 during epithelial development coincides with the onset of stratification. Int J Dev Biol 1999; 43(3):229-35.
52. Ueda S, Kuwabara I, Liu F T. Suppression of tumor growth by galectin-7 gene transfer. Cancer Res 2004; 64(16):5672-6.
53. Valencia X, Lipsky P E. CD4+CD25+FoxP3+ regulatory T cells in autoimmune diseases. Nat Clin Pract Rheumatol 2007; 3(11):619-26.
54. Van Belle A B, de Heusch M, Lemaire M M, Hendrickx E, Warnier G, Dunussi-Joannopoulos K, et al. IL-22 is required for imiquimod-induced psoriasiform skin inflammation in mice. J Immunol. 2012; 188(1):462-9.
55. van Kooyk Y, Rabinovich G A. Protein-glycan interactions in the control of innate and adaptive immune responses. Nat immunol 2008; 9(6):593-601.
56. Vignali D A, Collison L W, Workman C J. How regulatory T cells work. Nat Rev Immunol 2008; 8(7):523-32.
57. Yang R Y, Rabinovich G A, Liu F T. Galectins: structure, function and therapeutic potential. Expert Rev Mol Med. 2008; 10:e17.
58. Wang L, Bursch L S, Kissenpfennig A, Malissen B, Jameson S C, Hogquist K A. Langerin expressing cells promote skin immune responses under defined conditions. J immunol 2008; 180(7):4722.

What is claimed is:

1. A method for treating psoriasis comprising, administering to an individual in need thereof an effective amount of Gal-7, thereby treating the psoriasis.

2. The method of claim 1, wherein the administration is transdermal.

3. The method of claim 1, wherein the Gal-7 is a recombinant protein and has the amino acid sequence of SEQ ID NO:1.

4. The method of claim 1, wherein the administration of an effective amount increases dermal regulatory T lymphocytes in the patient.

5. The method of claim 4, wherein the administration of an effective amount activates Langerhans cells to stimulate T-cell differentiation to regulatory T lymphocytes in the patient.

* * * * *